United States Patent
Khodabocus et al.

(10) Patent No.: US 7,642,352 B2
(45) Date of Patent: Jan. 5, 2010

(54) PROCESS FOR PREPARING 2,3-DISUBSTITUTED INDOLES

(75) Inventors: Ahmad Khodabocus, Richmond, VA (US); Zhi-Hui Lu, Glen Allen, VA (US); Chris Hugh Senanayake, Brookfield, CT (US); Hanxun Wei, Somerville, MA (US); Yongda Zhang, Richmond, VA (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 244 days.

(21) Appl. No.: 11/351,411

(22) Filed: Feb. 10, 2006

(65) Prior Publication Data

US 2006/0183752 A1  Aug. 17, 2006

Related U.S. Application Data

(60) Provisional application No. 60/652,072, filed on Feb. 11, 2005.

(51) Int. Cl.
C07D 403/04 (2006.01)

(52) U.S. Cl. .................................... 544/333

(58) Field of Classification Search ............ 514/255.05, 514/256, 337, 414, 394; 544/333, 405; 546/277.4; 548/465, 305.1
See application file for complete search history.

(56) References Cited

U.S. PATENT DOCUMENTS

| 7,141,574 B2 | 11/2006 | Beaulieu et al. |
| 7,157,486 B2 | 1/2007 | Beaulieu et al. |
| 2004/0024190 A1 | 2/2004 | Beaulieu et al. |
| 2004/0171833 A1 | 9/2004 | Buchwald et al. |
| 2005/0032875 A1 | 2/2005 | Wolleb et al. |
| 2005/0209465 A1 | 9/2005 | Li et al. |
| 2005/0222236 A1 | 10/2005 | Tsantrizos et al. |
| 2005/0234242 A1 | 10/2005 | Khodabocus et al. |
| 2006/0160798 A1 | 7/2006 | Beaulieu et al. |
| 2006/0293306 A1 | 12/2006 | Beaulieu et al. |
| 2009/0087409 A1 | 4/2009 | Beaulieu et al. |

FOREIGN PATENT DOCUMENTS

| WO | WO 03/007945 A1 | 1/2003 |
| WO | WO 03/010140 A2 * | 2/2003 |
| WO | WO 03/010141 A2 | 2/2003 |
| WO | WO03/018555 A | 3/2003 |
| WO | WO 2004/064925 A1 * | 8/2004 |
| WO | WO2004/065367 A1 | 8/2004 |
| WO | WO2005/012288 A | 2/2005 |
| WO | WO2005/080388 A | 9/2005 |

OTHER PUBLICATIONS

Watanabe, T., et al. "Synthesis of sterically hindered biaryls via the palladium-catalyzed cross-coupling reaction of arylboronic acids or their esters with haloarenes" SYNLETT, vol. 3, p. 207-210, 1992.

Merlic, C.A., et al. "Benzannulation reactions of Fischer carbene complexes for the synthesis of indolocarbozoles" TETRAHEDRON, vol. 57, No. 24, p. 5199-5212, 2001.

T. Ishiyama, et al. "Palladium (0)-Catalyzed Cross-Coupling Reaction of Alkoxydiboron with Haloarenes: A Direct Procedure for Arylboronic Esters", J. Org. Chem. 1995, vol. 60, pp. 7508-7510.

M. Murata, et al. "Palladium-Catalyzed Borylation of Aryl Halides or Triflates with Dialkoxyborane: A Novel and Facile Synthetic Route to Arylboronates", J. Org. Chem. 2000, vol. 65, pp. 164-168.

L. C. Rorreer, et al. "A Convenient New Route to Tetradentate and Pentadentate Macrocyclic Tetraamide Ligands", Organic Letters, 1999, vol. 1, No. 8, pp. 1157-1159.

N. Miyaura, et al. "Palladium_Catalyzed Cross-Coupling Reactions of Organoboron Compounds", Chem. Rev. 1995, vol. 95, pp. 2457-2483.

* cited by examiner

*Primary Examiner*—Kamal A Saeed
*Assistant Examiner*—Kristin Bianchi
(74) *Attorney, Agent, or Firm*—Michael P. Morris; Mary-Ellen M. Devlin; David A. Dow

(57) ABSTRACT

Disclosed are processes for making 2,3 disubstituted indole compounds such as compounds of general formula I comprised of the steps of a) reacting a bromoindole compound (i) with a dialkoxyl $C_{1-5}$ borane in the presence of a ligand, a palladium catalyst and a base to make a compound of general formula (ii); or alternatively reacting compound (i) with a trialkyl magnesiate reagent, followed by treatment with a borate;

b) reacting the product of step a with a R2-Hal where R2-Hal is defined herein.

6 Claims, No Drawings

PROCESS FOR PREPARING 2,3-DISUBSTITUTED INDOLES

RELATED APPLICATIONS

This application claims benefit to U.S. Provisional application No. 60/652,072 filed Feb. 11, 2005 the contents of which are incorporated herein.

BACKGROUND OF THE INVENTION

1. Technical Field

The invention relates to a process for the preparation 2,3 disubstituted indoles useful as pharmaceutical agents and particularly pharmaceutical agents for the treatment of hepatitis C viral (HCV) infections.

2. Background Information

Substituted indoles are useful as pharmaceutical agents. Examples of substituted indoles used as pharmaceutical agents thereof include the anti-inflammatory agents indomethacin and tropesin, the antihistamine mebhydroline, and the vasodilator vinpocetine. Other examples of indole compounds used as pharmaceutical agents are indole compounds such as disclosed in U.S. patent application Ser. No. 10/198,384 filed Jul. 7, 2002 and U.S. provisional application 60/546,213, filed Feb. 20, 2004.

One of the key aspects in the synthesis of disubstituted indoles is the coupling of the substituents at the 2,3 positions of the indole and a number of general methods have been used to perform the coupling. One method was exemplified by employing a dipyridyl zinc intermediate and a palladium catalyst as shown in U.S. provisional patent application No. 60/551,107 filed Mar. 8, 2004. This process is referred to herein as Process A.

PROCESS A

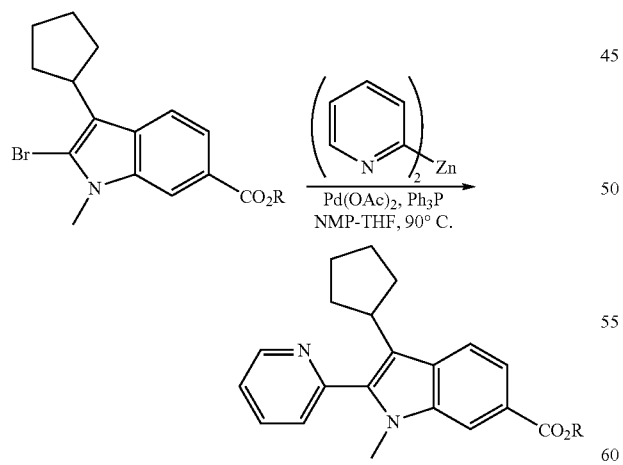

Another approach employs the use of Pd-catalyzed indolization of 2-bromo- or chloro-anilines with internal alkynes and is described in U.S. provisional patent application No. 60/553,596, filed Mar. 16, 2004. This process is referred herein as Process B

PROCESS B

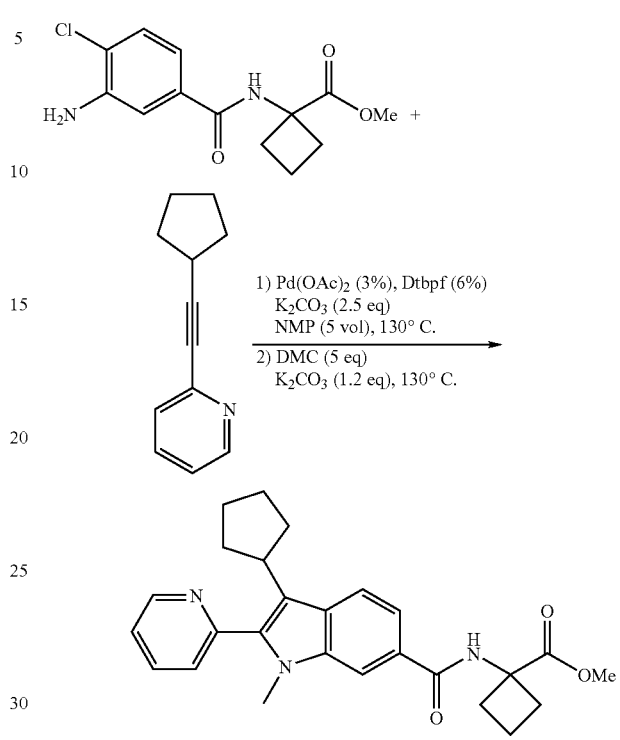

Although Processes A and B can be used in the preparation 2,3 disubstituted indoles both processes have some limitations. When the product contains the moiety of arylbromide as in the case shown below, Process A can potentially result in the formation of polymerization product from the competing side reaction of the desired product with the nucleophile i.e. the zinc reagent.

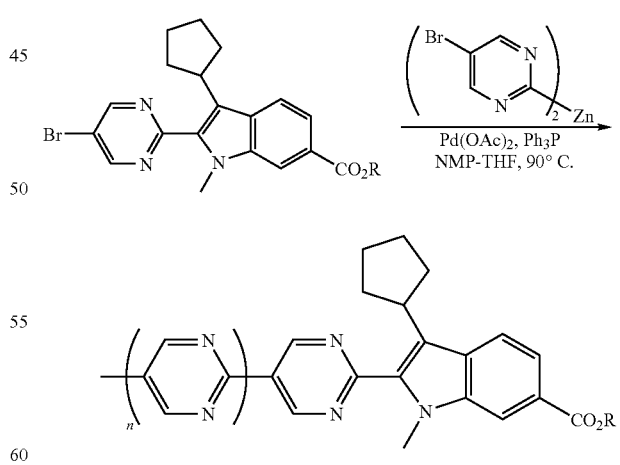

Similarly, when the substitutents of the internal alkynes contain the moiety of vinyl bromide, vinyliodide, arylbromide and aryliodide that would compete with 2-halogenanilines for oxidative insertion to the palladium catalyst, Process B can have poor efficiency.

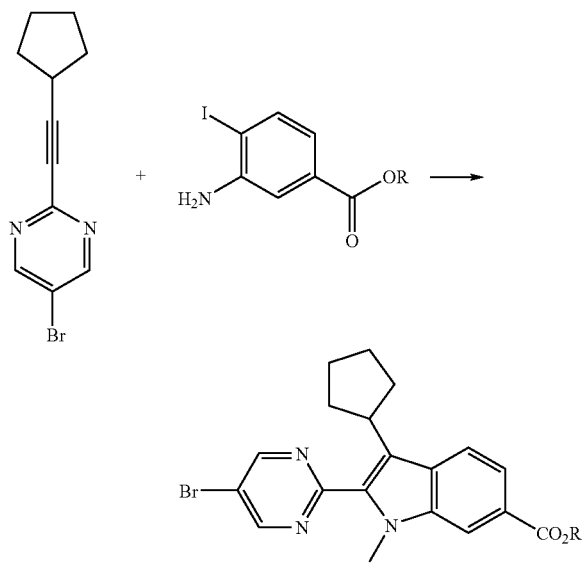

Synthetic routes for preparation of arylboronic esters 1-3 via palladium-catalyzed borylation were developed by Miyaura and Murata, by reaction of bis(pinacolato)diboron 1-1 with aryl halides [Ishiyama, T.; Murata, M.; Miyaura, N. *J. Org Chem.* 1995, 60, 7508], or from dialkoxyhydroborane 1-2 with aryl halides or triflates [Murata, M.; Oyama, T.; Watanabe, S., Masuda, Y. *J. Org Chem.* 2000, 65, 164]. However, optimal reaction conditions are often varied significantly, depending upon the structures of the substrates.

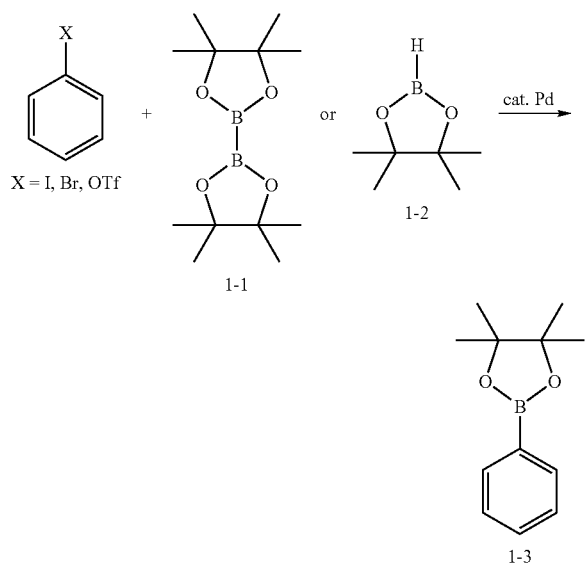

Therefore, design of new process for making 2,3 disubstituted indoles is needed in the art.

BRIEF SUMMARY OF THE INVENTION

The present invention provides a process for making 2,3 disubstituted indoles of general formula (I):

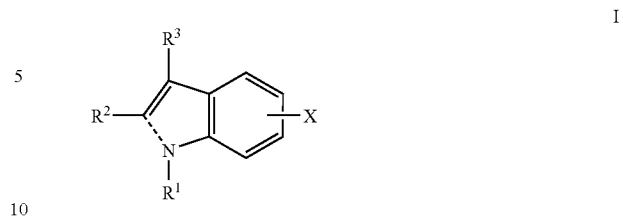

said method comprised of the steps of
a) reacting a bromoindole compound (i):

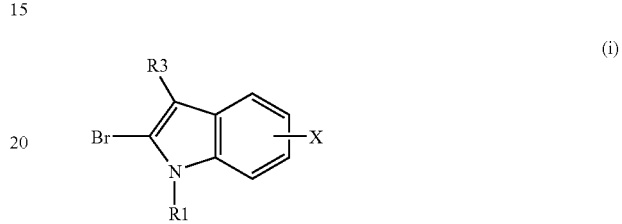

with a dialkoxyl $C_{1-5}$ borane in the presence of a ligand, a palladium catalyst and a base to make a compound of general formula (ii);

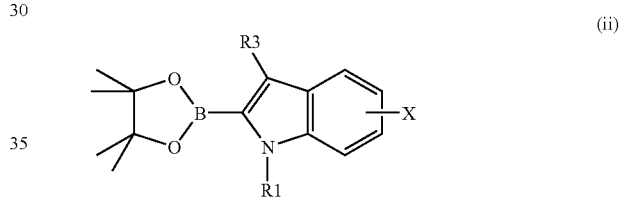

or alternatively reacting compound (i) with a trialkyl magnesiate reagent, followed by treatment with a borate to make a compound of general formula (ii) above;
b) reacting the product of step a with:

$R^2$-Hal to provide the desired product of general formula I:
wherein:
$R^1$, $R^2$ and $R^3$, X and Hal are defined herein.
The invention also relates to a process for making compounds of general formula III:

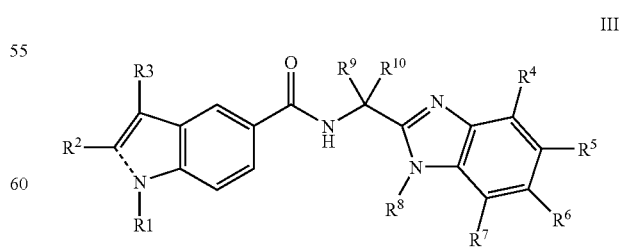

Wherein $R^1$-$R^{10}$ are defined herein.
The invention also provides compounds which are active as pharmaceutical agents such as HCV inhibitors and useful as intermediates in the synthesis of HCV inhibitors in making intermediates of said compounds.

DETAILED DESCRIPTION OF THE INVENTION

Definitions and Terms

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $(C_{1-8})$alkyl means an alkyl group or radical having 1 to 8 carbon atoms and $(C_{3-7})$cycloalkyl means a cycloalkyl group having from 3 to 7 carbon atoms in the ring. In general, for groups comprising two or more subgroups, the last named group is the radical attachment point, for example, "cycloalkylalkyl" means a monovalent radical of the formula cycloalkyl-alkyl- and phenylalkyl means a monovalent radical of the formula phenyl-alkyl-. Unless otherwise specified below, conventional definitions of terms control and conventional stable atom valences are presumed and achieved in all formulas and groups.

The term "alkyl" as used herein, either alone or in combination with another substituent, means acyclic, straight or branched chain alkyl substituents containing the specified number of carbon atoms.

The term "alkoxy" as used herein, either alone or in combination with another substituent, means an alkyl group as defined above linked as a substituent through an oxygen atom: alkyl-O—.

In general, all tautomeric forms and isomeric forms and mixtures, whether individual geometric isomers or optical isomers or racemic or non-racemic mixtures of isomers, of a chemical structure or compound are intended, unless the specific stereochemistry or isomeric form is specifically indicated in the compound name or structure.

The term "pharmaceutically acceptable salt" as used herein includes those derived from pharmaceutically acceptable bases. Examples of suitable bases include choline, ethanolamine and ethylenediamine. $Na^+$, $K^+$, and $Ca^{++}$ salts are also contemplated to be within the scope of the invention (also see *Pharmaceutical Salts*, Birge, S. M. et al., J. Pharm. Sci., (1977), 66, 1-19, incorporated herein by reference).

The term "pharmaceutically acceptable ester" as used herein, either alone or in combination with another substituent, means esters of the compound of formula I in which any of the carboxyl functions of the molecule, but preferably the carboxy terminus, is replaced by an alkoxycarbonyl function:

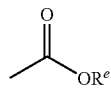

in which the Re moiety of the ester is selected from alkyl (e.g. methyl, ethyl, n-propyl, t-butyl, n-butyl); alkoxyalkyl (e.g. methoxymethyl); alkoxyacyl (e.g. acetoxymethyl); aralkyl (e.g. benzyl); aryloxyalkyl (e.g. phenoxymethyl); aryl (e.g. phenyl), optionally substituted with halogen, $C_{1-4}$ alkyl or $C_{1-4}$ alkoxy. Other suitable prodrug esters are found in *Design of Prodrugs*, Bundgaard, H. Ed. Elsevier (1985) incorporated herewith by reference. Such pharmaceutically acceptable esters are usually hydrolyzed in vivo when injected in a mammal and transformed into the acid form of the compound of formula I. With regard to the esters described above, unless otherwise specified, any alkyl moiety present advantageously contains 1 to 16 carbon atoms, particularly 1 to 6 carbon atoms. Any aryl moiety present in such esters advantageously comprises a phenyl group.

In particular the esters may be a $C_{1-16}$ alkyl ester, an unsubstituted benzyl ester or a benzyl ester substituted with at least one halogen, $C_{1-6}$ alkyl, $C_{1-6}$ alkoxy, nitro or trifluoromethyl.

The following chemicals may be referred to by these abbreviations:

TABLE I

| Abbreviation | Chemical Name |
|---|---|
| NMP | 1-methyl-2-pyrrolidinone |
| DMC | N,N'-dimethyl acetamide |
| PH3P | Triphenyl phosphine |
| Net₃ or Et₃N or TEA | Triethyl amine |
| TFP | Isopropyl alcohol |
| IPA | Dimethylaminopyridine |
| DMAP | N,N-Dimethylformamide |
| DMF | O-(Benzotriazol-1-yl)-N,N,N',N'-tetramethyluronium tetrafluoroborate |
| MTBE | Methyl tert-butyl ether |
| SEH | Sodium 2-ethylhexanoate |

General Synthetic Methods

In the synthetic schemes below, unless specified otherwise, all the substituent groups in the chemical formulas shall have the same meanings as in general Formula (I). The reactants used in the synthetic schemes described below may be obtained either as described herein, or if not described herein, are themselves either commercially available or may be prepared from commercially available materials by methods known in the art. Certain starting materials, for example, may be obtained by methods described in U.S. patent application No. 60/546,213 filed Feb. 20, 2004.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by High Pressure Liquid Chromatography (HPLC), if desired, and intermediates and products may be purified by chromatography on silica gel and/or by recrystallization.

I. Preparation of Bromoindoles

The following scheme shows a general method for preparing bromoindole starting materials for the inventive process.

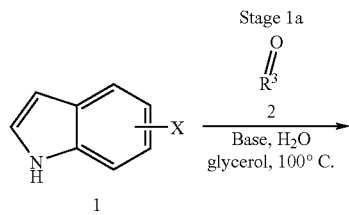

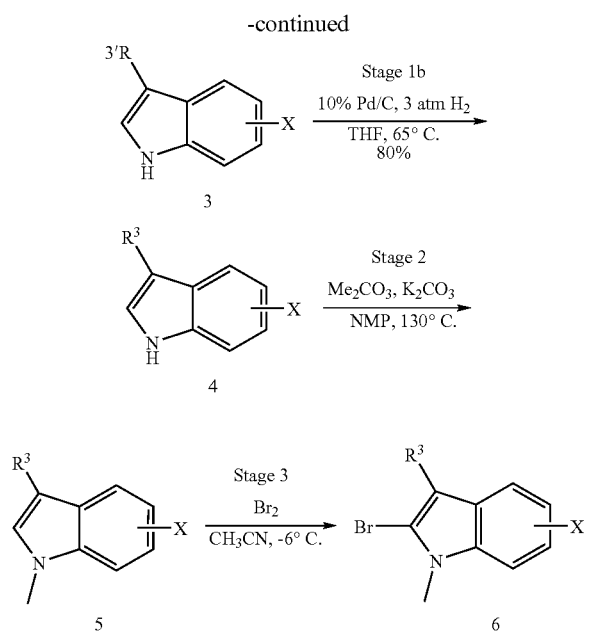

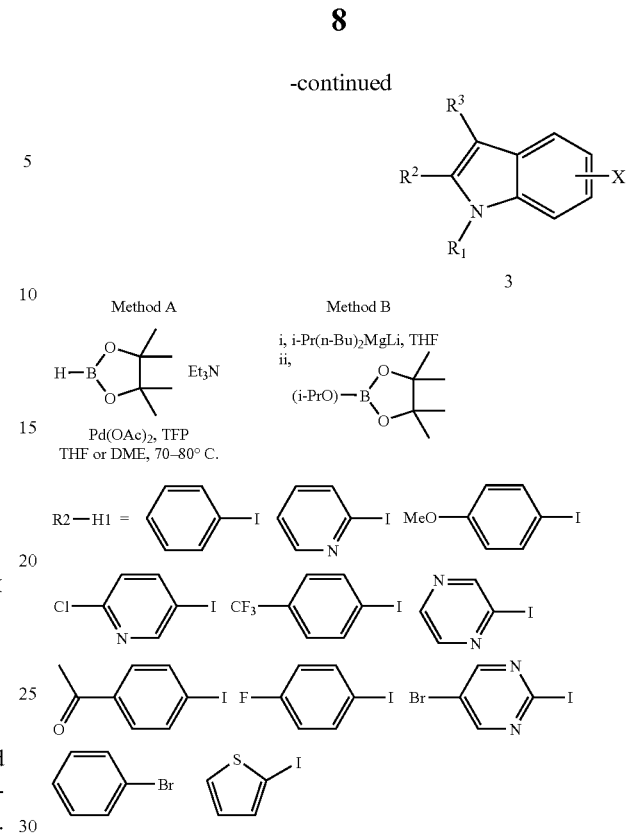

Condensation of an indole derivative (1) can be performed with a cycloalkylanone (2) compound such as cyclopropanone or cyclohexanone in the presence of an aqueous base. Suitable bases include aqueous sodium hydroxide can be used to prepare the 3-cycloalkenyl compound $R^{3'}$ (3), which can then be subjected to hydrogenation in the presence of a catalytic amount of palladium on carbon to afford the corresponding cycloalkyl indole derivative (4). In the event that the X substituent has an active species then protection of the active specifies may be necessary. For instance if X is a carboxylic acid group then methylation of the carboxylic acid group may be performed. Methylation of the Nitrogen on the indole ring can also be performed at this step. Bromination of the indole derivative with bromine in acetonitrile is then performed to furnish the 2-bromo-3-cycloalkyl indole product (6).

II. General Procedure for Making 2,3 Disubstituted Indoles from Bromoindoles

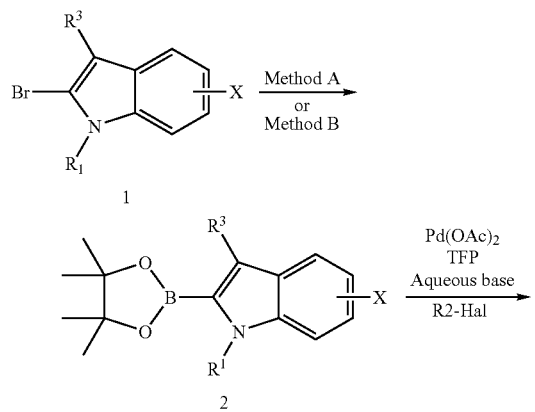

A bromoindole derivative compound (1) can be converted into a dialkylboronate indole derivate compound (2) by using either Method A which employs a dialkoxylborane in the presence of a ligand such as TFP, a palladium catalyst and a base. The preferred reaction conditions are as follows 1.2 equivalent of pinacolborane, 1.5 equivalent of Et3N, catalytic amount of Pd(OAc)2 (3 mol %) and tri(2-furyl)phosphine (12 mol %) in solvent such as DME, or THF. The reaction is performed at between 70-80° C.

Alternatively, Method B can be used to obtain product (2). Method B includes reacting a trialkylmagnesiate reagent followed by treatment with a borate. The range of acceptable conditions for this reaction are: treatment of bromoindole 1 with trialkylmagnesiate, such as iso-PrHex2MgLi (between 0.5 equivalent and 0.7 equivalent) at a temperature between −20° C. and 0° C., followed by subsequent addition of a borate such as 2-isopropoxy-4,4,5,5,-tetramethyl-1,3,2-dioxaborolane at 0° C. The indole derivative (2) can then be reacted with an iodo or bromo heterocyclic compound of general formula R2-Hal to provide the desired produce of general formula I.

Ligands—Ligand that can be used in the inventive process include tri(2-furyl)phosphine, allowing the Suzuki style coupling reaction to be carried out under mild conditions. The use of tri(2-furyl)phosphine also allows simple aqueous inorganic salts, such as $K_2CO_3$ or $K_3PO_4$ to be used. In addition, tri(2-furyl)phosphine can catalyze the first step process (borylation) as well, therefore, allowing the combination of the two-step sequence in one-pot reaction.

Magnesiate—another aspect of the inventive process relates to the use of the Br-metal exchange of the 2-bromoindole using a magnesiate. Examples of magnesiates that can be used include $G_{1-3}$ MgLi wherein G is any $C_{1-6}$ alkyl group. The preferred magnesiate is i-Pr(n-Hex)2MgLi or i-Pr(n-Bu)2MgLi etc. The use of the magnesiate in Method B can allow for the 2-indole anion to be readily generated at above −20° C. in the presence of a carboxylate functionality at the X position.

Bases—another aspect of the inventive process relates to the use of aqueous bases. Bases that can be used with the method of the invention include $K_2CO_3$ and $K_2PO_4$.

One pot reaction—In certain embodiments the inventive process can be performed as a "one-pot" process for preparation of 2,3-disubstituted indoles from 2-bromoindole intermediates via the palladium-catalyzed borylation and Suzuki coupling reactions. This process provides a way to make a variety of 2,3-disubstituted indoles without using the costly palladium catalyst two times. Tri(2-furyl)phosphine can be used as the common ligand for the two steps of the process, (i.e. the borylation and the Suzuki coupling reactions) and is the preferred ligand for the inventive process.

Preparation of Compounds of General Formula III

Indole derivatives according to general formula III such as those described in U.S. provisional application 60/546,213 and particularly those of Table 1 of the application can be synthesized according to this invention is preferably using the following the general procedure outlined in Scheme 1 below.

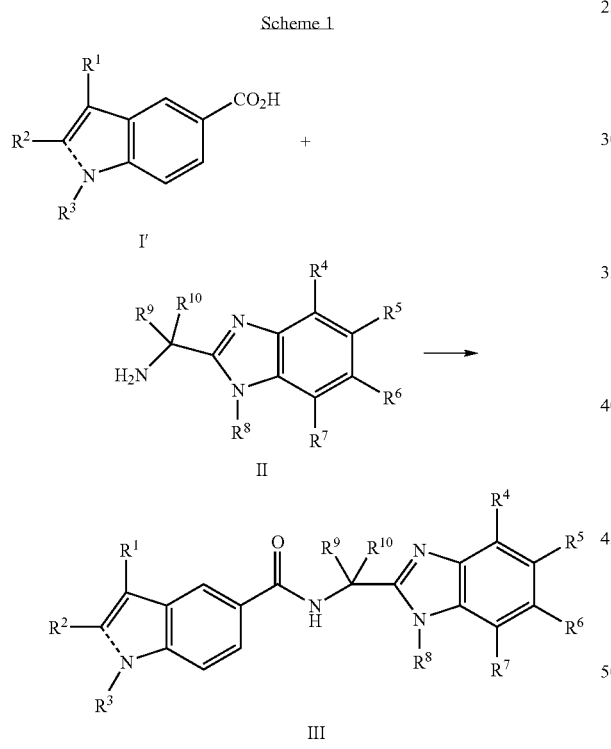

Compounds of general formula III, wherein $R^1$, $R^2$, $R^3$, $R^4$, $R^5$, $R^6$, $R^7$, $R^8$, $R^9$ and $R^{10}$ are defined as herein before, are preferably prepared by coupling carboxylic acids of general formula I' with amines of general formula II, as illustrated in Scheme 1 above, using carboxyl-activating reagents well known by those skilled in the art. Such reagents include, but are not limited to, TBTU, HATU, BOP, BrOP, EDAC, DCC, isobutyl chloroformate and the like. Alternatively, carboxylic acids of general formula I' may be converted to the corresponding acid chlorides using standard reagents, then coupled with amine derivatives of the general formula II. In the cases where either $R^5$ or $R^6$ contain an ester-protected carboxylic acid moiety, a saponification reaction is carried out (using protocols well known by those skilled in the art) to obtain the final inhibitor product as the free carboxylic acid.

Intermediate carboxylic acids of general formula I' may be prepared by procedures described in WO 03/010141, or by procedures described in the examples below. Intermediate amines of formula II may be prepared according to the general procedures outlined in Schemes 2 and 3 below.

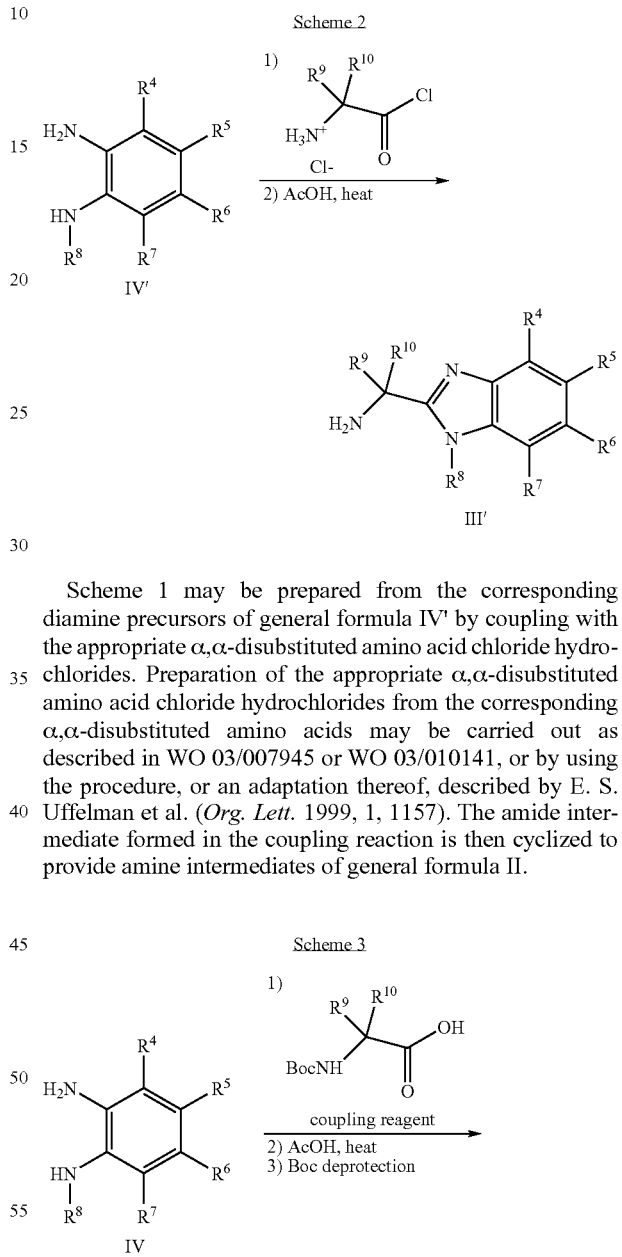

Scheme 1 may be prepared from the corresponding diamine precursors of general formula IV' by coupling with the appropriate α,α-disubstituted amino acid chloride hydrochlorides. Preparation of the appropriate α,α-disubstituted amino acid chloride hydrochlorides from the corresponding α,α-disubstituted amino acids may be carried out as described in WO 03/007945 or WO 03/010141, or by using the procedure, or an adaptation thereof, described by E. S. Uffelman et al. (*Org. Lett.* 1999, 1, 1157). The amide intermediate formed in the coupling reaction is then cyclized to provide amine intermediates of general formula II.

Alternatively, amine intermediates of general, formula II in Scheme 1 may be prepared from the corresponding diamine precursors of general formula IV by coupling with the appropriate Boc-protected α,α-disubstituted amino acid as illustrated in Scheme 3, using coupling reagents well known to one skilled in the art, such as TBTU, HATU, BOP, BrOP, EDAC, DCC, isobutyl chloroformate and the like. Appropriate Boc-protected α,α-disubstituted amino acids may be prepared from the free α,α-disubstituted amino acids, using standard conditions well known to one skilled in the art, such as reaction with $Boc_2O$ in the presence of a tertiary amine such as triethylamine, and the like. The amide intermediate formed in the coupling reaction is then cyclized by heating in the presence of an acid such as acetic acid, or hydrochloric acid. Deprotection of the Boc group to provide the amine intermediate of general formula II in Scheme 1 is carried out using standard reagents well known to one skilled in the art. Such reagents include, but are not limited to, trifluoroacetic acid, a solution of HCl in dioxane and the like.

Preparation of the diamine precursors of general formula IV in Schemes 2 and 3 is preferably carried out by applying the procedures as outlined in the examples, including any adaptation of these procedures, and/or applying additional synthetic steps known to the person skilled in the art.

Amine intermediates of general formula II in Scheme 1 wherein one of $R^5$ and $R^6$ is —CH=C($R^{50}$)—COOR, wherein $R^{50}$ is selected from $(C_{1-6})$alkyl and halogen and wherein R is, for example, methyl or ethyl, may be prepared from the corresponding amine intermediates of general formula III, or suitably protected derivatives thereof, wherein one of $R^5$ and $R^6$ is —COOR, wherein R is, for example, methyl or ethyl, by applying the procedures of Scheme 4 below. While Scheme 4 specfically illustrates the preparation of amine intermediates of general formula II wherein $R^5$ is —CH=C($R^{50}$)—COOR, it is understood by the person skilled in the art that when $R^6$ is —COOR, the illustrated procedures, or adaptations thereof, will result in a product wherein $R^6$ is —CH=C($R^{50}$)—COOR. Also, it is understood by the person skilled in the art that the procedures of Scheme 4, or adaptations thereof, may also be used when converting a diamine precursor of general formula IV' in Schemes 2 and 3 above, or a suitably protected derivative thereof, or a suitable intermediate in its preparation, wherein one of $R^5$ and $R^6$ is —COOR, to a diamine precursor of general formula IV', or a suitably protected derivative thereof, or a suitable intermediate in its preparation wherein one of $R^5$ and $R^6$ is —CH=C($R^{50}$)—COOR, wherein $R^{50}$ and R defined as hereinbefore.

Scheme 4

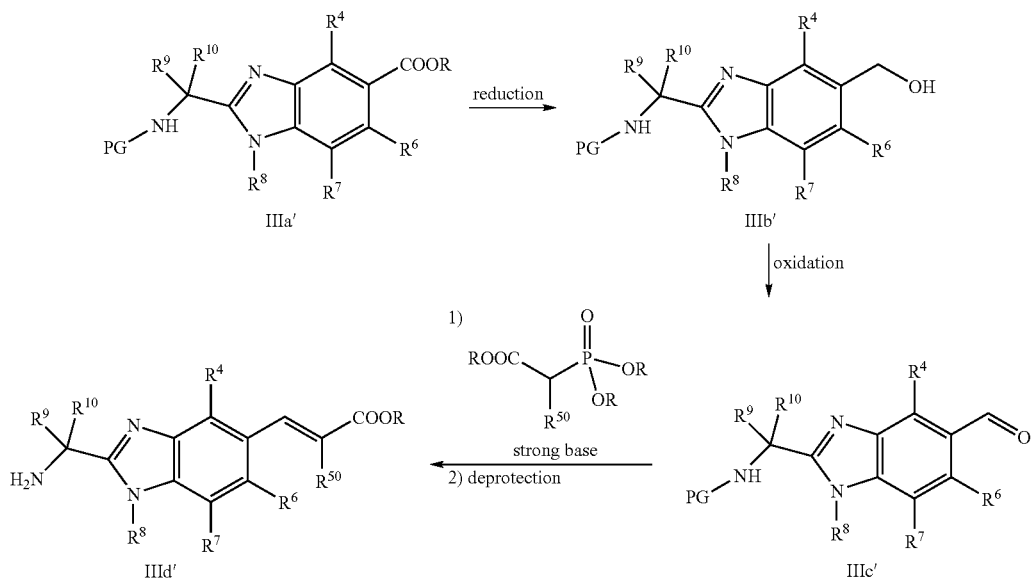

A suitably protected amine intermediate of general formula IIIa' in Scheme 4 above may be converted to an alcohol intermediate of general formula IIIb' by treatment with a suitable reducing agent such as DIBAL-H and the like. Suitable protecting groups (PG) include, but are not limited to, carbamate protecting groups, such as Boc (tert-butyloxycarbonyl) and the like. Preparation of protected amine intermediates of general formula IIIa from amine intermediates of general formula II in Scheme 1 above may be carried out by standard procedures well-known to one skilled in the art.

The alcohol intermediate IIIb' may be converted to the aldehyde intermediate IIIc', using standard oxidizing agents well-known to one skilled in the art, such as 1,1,1-tris(acetyloxy-1,1-dihydro-1,2-benziodoxol-3-(1H)-one (also known as Dess-Martin periodinane) and the like.

The aldehyde intermediate IIIc' may be converted to an amine intermediate of general formula IIId' using a standard Horner-Emmons procedure, or related procedures such as Wittig procedures or the like, well known to a person skilled in the art, followed by deprotection of the PG group using well-known standard procedures. In the case where the PG group is Boc, such procedures include, but are not limited to, treatment with acidic conditions such as trifluoroacetic acid, HCl dissolved in dioxane and the like.

Pharmaceutically acceptable salts of compound disclosed herein could include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N-$(C_1$-$C_4$ alkyl$)_4^+$ salts.

EMBODIMENTS OF THE INVENTION

A first embodiment of the invention provides a process for making 2,3 disubstituted indoles of general formula (I):

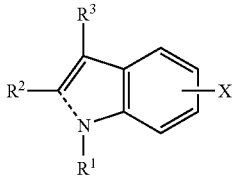

said method comprised of the steps of
a) reacting a bromoindole compound (i):

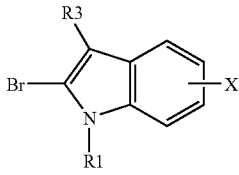

with a dialkoxyl $C_{1-5}$ borane in the presence of a ligand, a palladium catalyst and a base to make a compound of general formula ii;

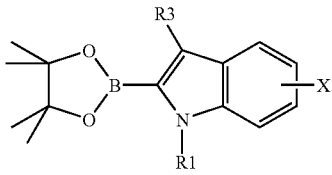

or alternatively reacting compound (i) with a trialkyl magnesiate reagent, followed by treatment with a borate to make a compound of general formula ii above;
b) reacting the product of step a with:

R2-Hal to provide a compound of general formula I;
wherein:
$R^1$ is H or $(C_{1-6})$alkyl;
$R^2$ is Het; or aryl having 5 or 6 members and Het or aryl being optionally substituted with $R^{21}$;
wherein $R^{21}$ is one, two or three substituents selected from —OH, —CN, —N$(R^{N2})R^{N1}$, halogen, $(C_{1-6})$alkyl, $(C_{1-6})$alkoxy, $(C_{1-6})$alkylthio, Het and —CO—N$(R^{N2})$R$^{N1}$;

wherein said alkyl, alkoxy and alkylthio are each optionally substituted with one, two or three halogen atoms;
$R^3$ is $(C_{5-6})$cycloalkyl, optionally substituted with from one to four halogen atoms;
X is: H, $C_{1-6}$ alkyl, $C_{1-6}$ alkoxy;

Hal is Br or I
L is H or a group further comprised of general formula iii:

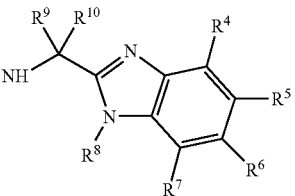

wherein
$R^4$ and $R^7$ are each independently selected from H, $(C_{1-6})$alkyl, $(C_{1-6})$alkoxy, $(C_{1-6})$alkylthio, —NH$_2$, —NH$(C_{1-6})$alkyl, —N$((C_{1-6})$alkyl$)_2$ and halogen;
One of $R^5$ and $R^6$ is selected from COOH, —CO—N$(R^{N2})$R$^{N1}$, Het$^1$ and $(C_{2-6})$alkenyl, wherein Het$^1$, $(C_{2-6})$alkenyl and R$^{N1}$ or any heterocycle formed between R$^{N2}$ and R$^{N1}$ is optionally substituted with R$^{50}$;
wherein R$^{50}$ is one, two or three substituents selected from $(C_{1-6})$alkyl, —COOH, —N$(R^{N2})R^{N1}$, —CO—N$(R^{N2})$R$^{N1}$, and halogen;
and the other of $R^5$ and $R^6$ is selected from H, $(C_{1-6})$alkyl, $(C_{1-6})$alkoxy, $(C_{1-6})$alkylthio, and N$(R^{N2})R^{N1}$;
$R^8$ is $(C_{1-6})$alkyl, $(C_{3-7})$cycloalkyl or $(C_{3-7})$cycloalkyl-$(C_{1-6})$alkyl-;
wherein said alkyl, cycloalkyl and cycloalkyl-alkyl are optionally substituted with one, two or three substituents selected from halogen, $(C_{1-6})$alkoxy and $(C_{1-6})$alkylthio;
$R^9$ and $R^{10}$ are each independently selected from $(C_{1-6})$alkyl; or $R^9$ and $R^{10}$ are covalently bonded together to form $(C_{3-7})$cycloalkyl, $(C_{5-7})$cycloalkenyl or a 4-, 5- or 6-membered heterocycle having from 1 to 3 heteroatoms selected from O, N, and S; wherein said cycloalkyl, cycloalkenyl or heterocycle is optionally substituted with $(C_{1-4})$alkyl;
$R^{N1}$ is selected from H, $(C_{1-6})$alkyl, $(C_{3-7})$cycloalkyl, $(C_{3-7})$cycloalkyl-$(C_{1-6})$alkyl-, —CO—$(C_{1-6})$alkyl, —CO—O—$(C_{1-6})$alkyl and Het$^1$;
wherein all of said alkyl and cycloalkyl is optionally substituted with one, two or three substituents selected from halogen, $(C_{1-6})$alkoxy and $(C_{1-6})$alkylthio; and
$R^{N2}$ is H or $(C_{1-6})$alkyl, or
$R^{N2}$ and $R^{N1}$ may be covalently bonded together to form a 4-, 5-, 6- or 7-membered saturated or unsaturated N-containing heterocycle or a 8-, 9-, 10- or 11-membered N-containing heterobicycle, each having additionally from 1 to 3 heteroatoms selected from O, N, and S;
wherein the heterocycle or heterobicycle formed by $R^{N2}$ and $R^{N1}$ is optionally substituted with one, two or three substituents selected from halogen, $(C_{1-6})$alkyl, $(C_{1-6})$alkoxy and $(C_{1-6})$alkylthio;

wherein Het is defined as a 4-, 5-, 6- or 7-membered heterocycle having 1 to 4 heteroatoms selected from O, N and S, which may be saturated, unsaturated or aromatic, or a 8-, 9-, 10- or 11-membered heterobicycle having 1 to 5 heteroatoms wherever possible, selected from O, N and S, which may be saturated, unsaturated or aromatic;

or a pharmaceutically acceptable salt thereof

A second embodiment of the invention provides a method for making 2,3 disubstituted indoles of general formula (I) wherein $R^1$ is H or $(C_{1-6})$alkyl;

$R^2$ is Het; or aryl having 5 or 6 members and Het or aryl being optionally substituted with $R^{21}$;

wherein $R^{21}$ is one, two or three substituents selected from —OH, —CN, —N($R^{N2}$)$R^{N1}$, halogen, $(C_{1-6})$alkyl, $(C_{1-6})$alkoxy, $(C_{1-6})$alkylthio, Het and —CO—N($R^{N2}$)$R^{N1}$;

wherein said alkyl, alkoxy and alkylthio are each optionally substituted with one, two or three halogen atoms;

R3 is cyclopentyl;

X is: H, $C_{1-6}$ alkyl, $C_{1-6}$ alkoxy,

Hal is I or Br;

L is H or a group further comprised of general formula iii:

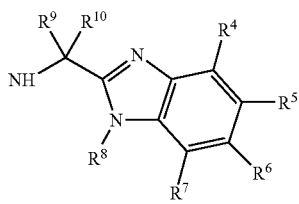

iii wherein $R^4$ and $R^7$ are each independently selected from H, $(C_{1-6})$alkyl, $(C_{1-6})$alkoxy, $(C_{1-6})$alkylthio, —NH$_2$, —NH$(C_{1-6})$alkyl, —N$((C_{1-6})$alkyl$)_2$ and halogen;

One of $R^5$ and $R^6$ is selected from COOH, —CO—N($R^{N2}$)$R^{N1}$, Het$^1$ and $(C_{2-6})$alkenyl, wherein Het$^1$, $(C_{2-6})$alkenyl and $R^{N1}$ or any heterocycle formed between $R^{N2}$ and $R^{N1}$ is optionally substituted with $R^{50}$;

wherein $R^{50}$ is one, two or three substituents selected from $(C_{1-6})$alkyl, —COOH, N($R^{N2}$)$R^{N1}$—, —CO—N($R^{N2}$)$R^{N1}$, and halogen;

and the other of $R^5$ and $R^6$ is selected from H, $(C_{1-6})$alkyl, $(C_{1-6})$alkoxy, $(C_{1-6})$alkylthio, and N($R^{N2}$)$R^{N1}$;

$R^8$ is $(C_{1-6})$alkyl, $(C_{3-7})$cycloalkyl or $(C_{3-7})$cycloalkyl-$(C_{1-6})$alkyl-;

wherein said alkyl, cycloalkyl and cycloalkyl-alkyl are optionally substituted with one, two or three substituents selected from halogen, $(C_{1-6})$alkoxy and $(C_{1-6})$alkylthio;

$R^9$ and $R^{10}$ are each independently selected from $(C_{1-6})$alkyl; or $R^9$ and $R^{10}$ are covalently bonded together to form $(C_{3-7})$cycloalkyl, $(C_{5-7})$cycloalkenyl or a 4-, 5- or 6-membered heterocycle having from 1 to 3 heteroatoms selected from O, N, and S; wherein said cycloalkyl, cycloalkenyl or heterocycle is optionally substituted with $(C_{1-4})$alkyl;

$R^{N1}$ is selected from H, $(C_{1-6})$alkyl, $(C_{3-7})$cycloalkyl, $(C_{3-7})$cycloalkyl-$(C_{1-6})$alkyl-, —CO—$(C_{1-6})$alkyl, —CO—O—$(C_{1-6})$alkyl and Het$^1$;

wherein all of said alkyl and cycloalkyl is optionally substituted with one, two or three substituents selected from halogen, $(C_{1-6})$alkoxy and $(C_{1-6})$alkylthio; and $R^{N2}$ is H or $(C_{1-6})$alkyl, or $R^{N2}$ and $R^{N1}$ may be covalently bonded together to form a 4-, 5-, 6- or 7-membered saturated or unsaturated N-containing heterocycle or a 8-, 9-, 10- or 11-membered N-containing heterobicycle, each having additionally from 1 to 3 heteroatoms selected from O, N, and S;

wherein the heterocycle or heterobicycle formed by $R^{N2}$ and $R^{N1}$ is optionally substituted with one, two or three substituents selected from halogen, $(C_{1-6})$alkyl, $(C_{1-6})$alkoxy and $(C_{1-6})$alkylthio;

wherein Het is defined as a 4-, 5-, 6- or 7-membered heterocycle having 1 to 4 heteroatoms selected from O, N and S, which may be saturated, unsaturated or aromatic, or a 8-, 9-, 10- or 11-membered heterobicycle having 1 to 5 heteroatoms wherever possible, selected from O, N and S, which may be saturated, unsaturated or aromatic.

A third embodiment of the invention provides a method for making 2,3 disubstituted indoles of general formula (I) wherein $R^1$ is H or $(C_{1-6})$alkyl;

R2 is selected from

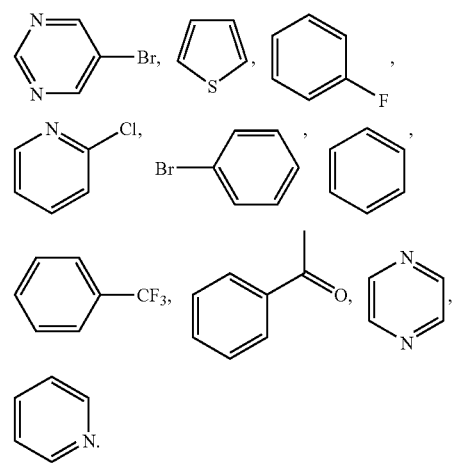

$R^3$ is $(C_{5-6})$cycloalkyl, optionally substituted with from one to four halogen atoms;

X is: H, $C_{1-6}$ alkyl, $C_{1-6}$ alkoxy,

Hal is Br or I;
L is H or a group further comprised of general formula iii:

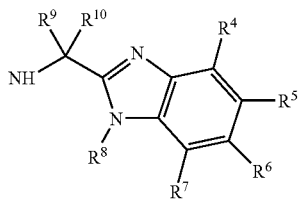

wherein
$R^4$ and $R^7$ are each independently selected from H, $(C_{1-6})$alkyl, $(C_{1-6})$alkoxy, $(C_{1-6})$alkylthio, —$NH_2$, —$NH(C_{1-6})$alkyl, —$N((C_{1-6})$alkyl$)_2$ and halogen;
One of $R^5$ and $R^6$ is selected from COOH, —CO_N($R^{N2}$)$R^{N1}$, $Het^1$ and $(C_{2-6})$alkenyl, wherein $Het^1$, $(C_{2-6})$alkenyl and $R^{N1}$ or any heterocycle formed between $R^{N2}$ and $R^{N1}$ is optionally substituted with $R^{50}$;
wherein $R^{50}$ is one, two or three substituents selected from $(C_{1-6})$alkyl, —COOH, —N($R^{N2}$)$R^{N1}$, —CO_N($R^{N2}$)$R^{N1}$, and halogen;
and the other of $R^5$ and $R^6$ is selected from H, $(C_{1-6})$alkyl, $(C_{1-6})$alkoxy, $(C_{1-6})$alkylthio, and N($R^{N2}$)$R^{N1}$;
$R^8$ is $(C_{1-6})$alkyl, $(C_{3-7})$cycloalkyl or $(C_{3-7})$cycloalkyl-$(C_{1-6})$alkyl-;
wherein said alkyl, cycloalkyl and cycloalkyl-alkyl are optionally substituted with one, two or three substituents selected from halogen, $(C_{1-6})$alkoxy and $(C_{1-6})$alkylthio;
$R^9$ and $R^{10}$ are each independently selected from $(C_{1-6})$alkyl; or $R^9$ and $R^{10}$ are covalently bonded together to form $(C_{3-7})$cycloalkyl, $(C_{5-7})$cycloalkenyl or a 4-, 5- or 6-membered heterocycle having from 1 to 3 heteroatoms selected from O, N, and S; wherein said cycloalkyl, cycloalkenyl or heterocycle is optionally substituted with $(C_{1-4})$alkyl;
$R^{N1}$ is selected from H, $(C_{1-6})$alkyl, $(C_{3-7})$cycloalkyl, $(C_{3-7})$cycloalkyl-$(C_{1-6})$alkyl-, —CO—$(C_{1-6})$alkyl, —CO—O—$(C_{1-6})$alkyl and $Het^1$;
wherein all of said alkyl and cycloalkyl is optionally substituted with one, two or three substituents selected from halogen, $(C_{1-6})$alkoxy and $(C_{1-6})$alkylthio; and
$R^{N2}$ is H or $(C_{1-6})$alkyl, or
$R^{N2}$ and $R^{N1}$ may be covalently bonded together to form a 4-, 5-, 6- or 7-membered saturated or unsaturated N-containing heterocycle or a 8-, 9-, 10- or 11-membered N-containing heterobicycle, each having additionally from 1 to 3 heteroatoms selected from O, N, and S;
wherein the heterocycle or heterobicycle formed by $R^{N2}$ and $R^{N1}$ is optionally substituted with one, two or three substituents selected from halogen, $(C_{1-6})$alkyl, $(C_{1-6})$alkoxy and $(C_{1-6})$alkylthio;
wherein Het is defined as a 4-, 5-, 6- or 7-membered heterocycle having 1 to 4 heteroatoms selected from O, N and S, which may be saturated, unsaturated or aromatic, or a 8-, 9-, 10- or 11-membered heterobicycle having 1 to 5 heteroatoms wherever possible, selected from O, N and S, which may be saturated, unsaturated or aromatic;

or a pharmaceutically acceptable salt thereof.
Another embodiment of the invention provides a method of claim 1 wherein $R^1$ is H or $(C_{1-6})$alkyl;
$R^2$ is Het; or aryl having 5 or 6 members and Het or aryl being optionally substituted with $R^{21}$;
wherein $R^{21}$ is one, two or three substituents selected from —OH, —CN, —N($R^{N2}$)$R^{N1}$, halogen, $(C_{1-5})$alkyl, $(C_{1-6})$alkoxy, $(C_{1-6})$alkylthio, Het and —CO—N($R^{N2}$)$R^{N1}$;
wherein said alkyl, alkoxy and alkylthio are each optionally substituted with one, two or three halogen atoms;
R3 is cyclopentyl;
X is carboxymethyl;
Hal is Br or I;
L is H or a group further comprised of general formula iii:

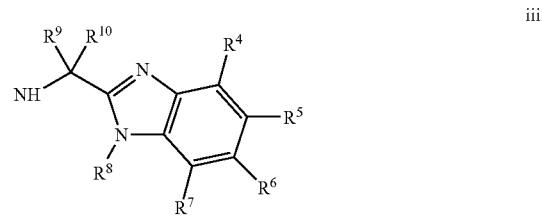

wherein
$R^4$ and $R^7$ are each independently selected from H, $(C_{1-6})$alkyl, $(C_{1-6})$alkoxy, $(C_{1-6})$alkylthio, —$NH_2$, —$NH(C_{1-6})$alkyl, —$N((C_{1-6})$alkyl$)_2$ and halogen;
One of $R^5$ and $R^6$ is selected from COOH, —CO—N($R^{N2}$)$R^{N1}$, $Het^1$ and $(C_{2-6})$alkenyl, wherein $Het^1$, $(C_{2-6})$alkenyl and $R^{N1}$ or any heterocycle formed between $R^{N2}$ and $R^{N1}$ is optionally substituted with $R^{50}$;
wherein $R^{50}$ is one, two or three substituents selected from $(C_{1-6})$alkyl, —COOH, —N($R^{N2}$)$R^{N1}$, —CO—N($R^{N2}$)$R^{N1}$, and halogen;
and the other of $R^5$ and $R^6$ is selected from H, $(C_{1-6})$alkyl, $(C_{1-6})$alkoxy, $(C_{1-6})$alkylthio, and N($R^{N2}$)$R^{N1}$;
$R^8$ is $(C_{1-6})$alkyl, $(C_{3-7})$cycloalkyl or $(C_{3-7})$cycloalkyl-$(C_{1-6})$alkyl-;
wherein said alkyl, cycloalkyl and cycloalkyl-alkyl are optionally substituted with one, two or three substituents selected from halogen, $(C_{1-6})$alkoxy and $(C_{1-6})$alkylthio;
$R^9$ and $R^{10}$ are each independently selected from $(C_{1-6})$alkyl; or $R^9$ and $R^{10}$ are covalently bonded together to form $(C_{3-7})$cycloalkyl, $(C_{5-7})$cycloalkenyl or a 4-, 5- or 6-membered heterocycle having from 1 to 3 heteroatoms selected from O, N, and S; wherein said cycloalkyl, cycloalkenyl or heterocycle is optionally substituted with $(C_{1-4})$alkyl;
$R^{N1}$ is selected from H, $(C_{1-6})$alkyl, $(C_{3-7})$cycloalkyl, $(C_{3-7})$cycloalkyl-$(C_{1-6})$alkyl-, —CO—$(C_{1-6})$alkyl, —CO—O—$(C_{1-6})$alkyl and $Het^1$;
wherein all of said alkyl and cycloalkyl is optionally substituted with one, two or three substituents selected from halogen, $(C_{1-6})$alkoxy and $(C_{1-6})$alkylthio; and
$R^{N2}$ is H or $(C_{1-6})$alkyl, or
$R^{N2}$ and $R^{N1}$ may be covalently bonded together to form a 4-, 5-, 6- or 7-membered saturated or unsaturated N-containing heterocycle or a 8-, 9-, 10- or 11-membered N-containing heterobicycle, each having additionally from 1 to 3 heteroatoms selected from O, N, and S;
wherein the heterocycle or heterobicycle formed by $R^{N2}$ and $R^{N1}$ is optionally substituted with one, two or three substituents selected from halogen, $(C_{1-6})$alkyl, $(C_{1-6})$alkoxy and $(C_{1-6})$alkylthio;

wherein Het is defined as a 4-, 5-, 6- or 7-membered heterocycle having 1 to 4 heteroatoms selected from O, N and S, which may be saturated, unsaturated or aromatic, or a 8-, 9-, 10- or 11-membered heterobicycle wherever possible, selected from O, N and S, which may be saturated, unsaturated or aromatic.

Another embodiment of the invention provides a method for making the compounds of general formula III:

III said method comprised of the steps of:
a) reacting a bromoindole compound (iv):

(iv)

with a dialkoxyl borane in the presence of a ligand and a palladium catalyst and a base to obtain compound of general formula (v);

(v)

b) reacting the product of step a with:

R2-Hal to provide the desired product of general formula III
wherein:
$R^1$ is H or $(C_{1-6})$alkyl;
$R^2$ is Het; or aryl having 5 or 6 members and Het or aryl being optionally substituted with $R^{21}$;
  wherein $R^{21}$ is one, two or three substituents selected from —OH, —CN, —N($R^{N2}$)$R^{N1}$, halogen, $(C_{1-6})$alkyl, $(C_{1-6})$alkoxy, $(C_{1-6})$alkylthio, Het and —CO_N($R^{N2}$)$R^{N1}$;
    wherein said alkyl, alkoxy and alkylthio are each optionally substituted with one, two or three halogen atoms;
$R^3$ is $(C_{5-6})$cycloalkyl, optionally substituted with from one to four halogen atoms;
X is: H, C1-C6 alkyl, C1 C6 alkoxy, Hal is Br or I;
L is H or a group further comprised of general formula iii:

iii wherein
$R^4$ and $R^7$ are each independently selected from H, $(C_{1-6})$alkyl, $(C_{1-6})$alkoxy, $(C_{1-6})$alkylthio, —NH$_2$, —NH$(C_{1-6})$alkyl, —N$((C_{1-6})$alkyl$)_2$ and halogen;
One of $R^5$ and $R^6$ is selected from COOH, —CO—N($R^{N2}$)$R^{N1}$, Het$^1$ and $(C_{2-6})$alkenyl, wherein Het$^1$, $(C_{2-6})$alkenyl and $R^{N1}$ or any heterocycle formed between $R^{N2}$ and $R^{N1}$ is optionally substituted with $R^{50}$;
  wherein $R^{50}$ is one, two or three substituents selected from $(C_{1-6})$alkyl, —COOH, —N($R^{N2}$)$R^{N1}$, —CO—N($R^{N2}$)$R^{N1}$, and halogen;
and the other of $R^5$ and $R^6$ is selected from H, $(C_{1-6})$alkyl, $(C_{1-6})$alkoxy, $(C_{1-6})$alkylthio, and N($R^{N2}$)$R^{N1}$;
$R^8$ is $(C_{1-6})$alkyl, $(C_{3-7})$cycloalkyl or $(C_{3-7})$cycloalkyl-$(C_{1-6})$alkyl-;
  wherein said alkyl, cycloalkyl and cycloalkyl-alkyl are optionally substituted with one, two or three substituents selected from halogen, $(C_{1-6})$alkoxy and $(C_{1-6})$alkylthio;
$R^9$ and $R^{10}$ are each independently selected from $(C_{1-6})$alkyl; or $R^9$ and $R^{10}$ are covalently bonded together to form $(C_{3-7})$cycloalkyl, $(C_{5-7})$cycloalkenyl or a 4-, 5- or 6-membered heterocycle having from 1 to 3 heteroatoms selected from O, N, and S;
  wherein said cycloalkyl, cycloalkenyl or heterocycle is optionally substituted with $(C_{1-4})$alkyl;
$R^{N1}$ is selected from H, $(C_{1-6})$alkyl, $(C_{3-7})$cycloalkyl, $(C_{3-7})$cycloalkyl-$(C_{1-6})$alkyl-, —CO—$(C_{1-6})$alkyl, —CO—O—$(C_{1-6})$alkyl and Het$^1$;
  wherein all of said alkyl and cycloalkyl is optionally substituted with one, two or three substituents selected from halogen, $(C_{1-6})$alkoxy and $(C_{1-6})$alkylthio; and
$R^{N1}$ is H or $(C_{1-6})$alkyl, or
$R^{N2}$ and $R^{N1}$ may be covalently bonded together to form a 4-, 5-, 6- or 7-membered saturated or unsaturated N-containing heterocycle or a 8-, 9-, 10- or 11-membered N-containing heterobicycle, each having additionally from 1 to 3 heteroatoms selected from O, N, and S;
  wherein the heterocycle or heterobicycle formed by $R^{N2}$ and $R^{N1}$ is optionally substituted with one, two or three substituents selected from halogen, $(C_{1-6})$alkyl, $(C_{1-6})$alkoxy and $(C_{1-6})$alkylthio;

wherein Het is defined as a 4-, 5-, 6- or 7-membered heterocycle having 1 to 4 heteroatoms selected from O, N and S, which may be saturated, unsaturated or aromatic, or a 8-, 9-, 10- or 11-membered heterobicycle having 1 to 5 heteroatoms wherever possible, selected from O, N and S, which may be saturated, unsaturated or aromatic.

Another embodiment of the invention provides a palladium-catalyzed borylation process wherein the dialkoxylborane is 4,4,5,5-tetramethyl-1,3,2-dioxaborolane.

Another embodiment of the invention provides a method for making compounds of general formula I wherein the borate used in the Br—Mg exchange process is isopropoxy-4,4,5,5-tetramethyl-1,3,2-dioxaborolane.

Another embodiment of the invention provides a method for making a compound of general formula I wherein step (a) is comprised of the step of reacting a bromoindole compound of formula (vi):

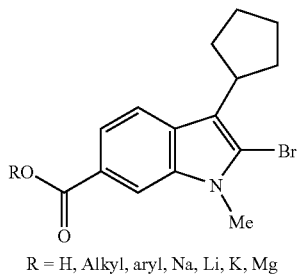

R = H, Alkyl, aryl, Na, Li, K, Mg with 4,4,5,5-tetramethyl-1,3,2-dioxaborolane to provide (vii)

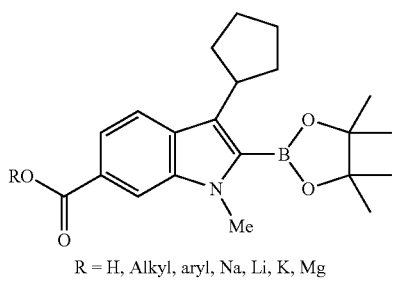

R = H, Alkyl, aryl, Na, Li, K, Mg b) reacting the product of step a with:

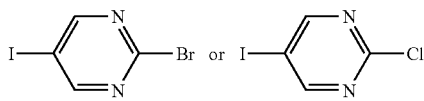

to provide:

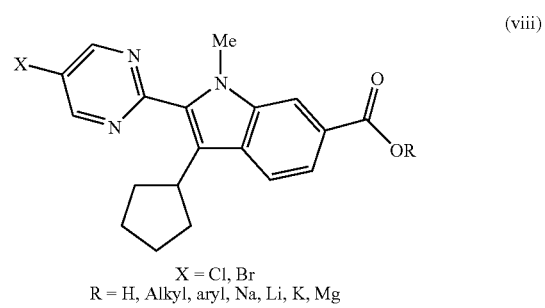

X = Cl, Br
R = H, Alkyl, aryl, Na, Li, K, Mg c) performing a hydrolysis with NaOH to provide (ix):

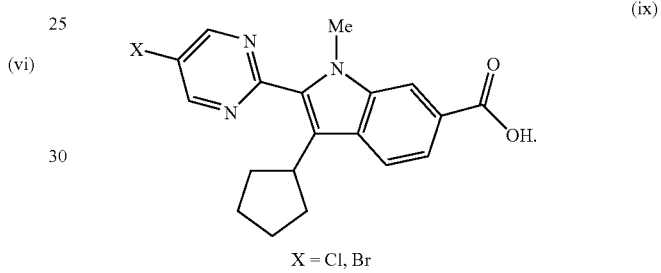

X = Cl, Br

In another embodiment of the invention the ligand is chosen from tri(2-furyl)phosphine and 2-(dicyclohexylphosphino)biphenyl for conversion of vi into vii by the Pd-catalyzed borylation process, and tri(2-furyl)phosphine for conversion of vii into viii by the Pd-catalyzed Suzuki coupling reaction.

In another embodiment of the invention the palladium catalyst is chosen from, $Pd(OAc)_2$, $PdCl_2$, $PdBr_2$, $Pd_2(dba)_3$, $Pd_2(dba)_3 \cdot CHCl_3$, $[Pd(ally)Cl]_2$, $Pd(CH_3CN)_2Cl_2$, $Pd(PhCN)_2Cl_2$, Pd/C and encapsulated Pd.

In another embodiment of the invention the solvent is DME, or THF and the base is triethylamine for the Pd-catalyzed borylation process that converts vi into vii. The solvent is DME, THF, or 2-propanol for the Suzuki coupling process and the base is potassium phosphate, or potassium carbonate.

In another embodiment of the invention the reagent for the bromo-magnesium exachange is trialkylmagnesiate is $G_{1-3}$MgLi wherein G is any $C_{1-6}$ alkyl group and preferably G1-3 MgLi chosen from i-Pr(n-Hex)$_2$MgLi or i-Pr(n-Bu)$_2$MgLi, n-Bu$_3$MgLi.

All references cited herein, including the journal articles or abstracts published or corresponding U.S. or foreign applications, issued or U.S. or foreign patents, or any other references, are entirely incorporated by reference herein, including any tables, figures and texts presented in the cited references.

SYNTHETIC EXAMPLES
The compounds shown in Table 1 were made according to the following examples.
TABLE 2
Example 1: One pot Borylation/Suzuki Coupling Process
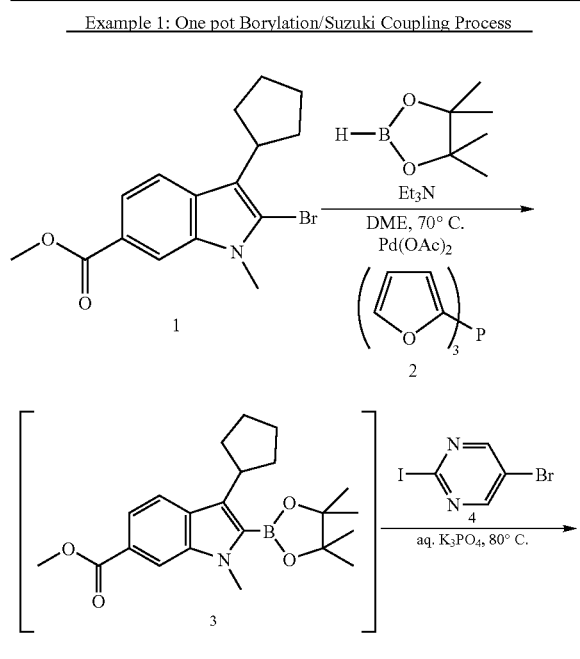
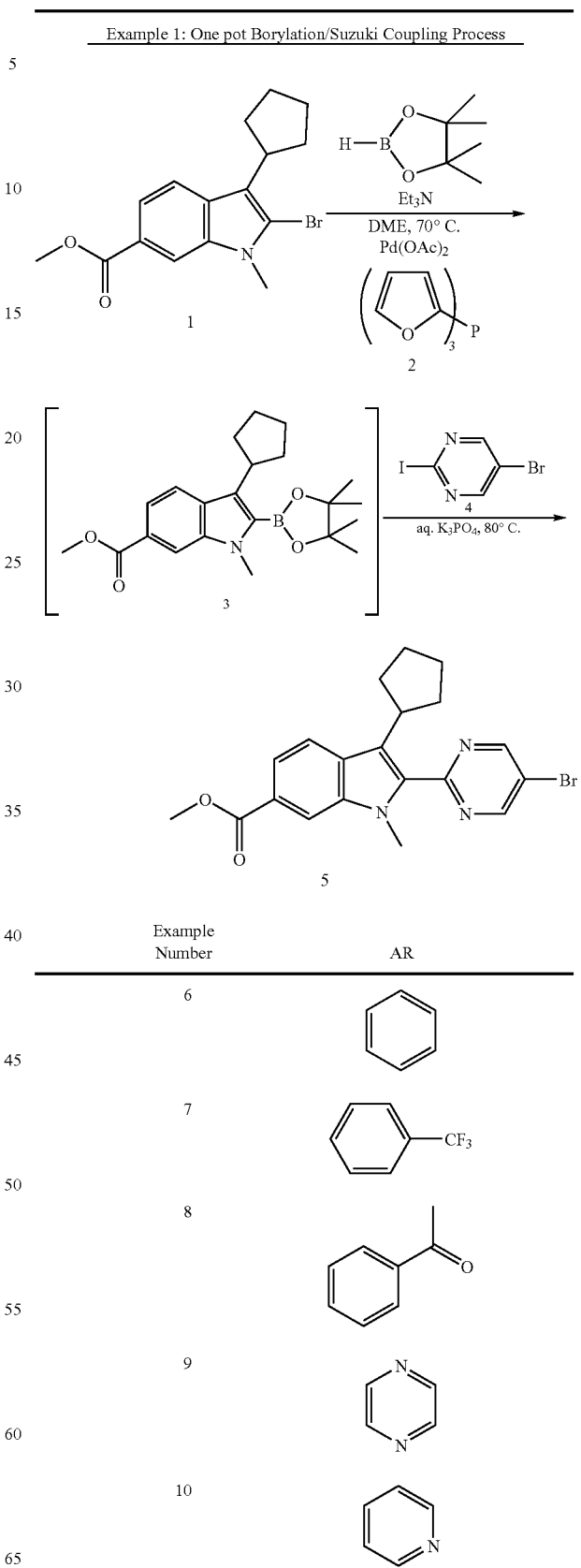
| Example Number | AR |
|---|---|
| 1 | 5-bromopyrimidin-2-yl |
| 2 | thiophen-2-yl |
| 3 | 3-fluorophenyl |
| 4 | 2-chloropyridin-? |
| 5 | 3-bromophenyl |
| 6 | phenyl |
| 7 | 4-(trifluoromethyl)phenyl |
| 8 | acetylphenyl |
| 9 | pyrazinyl |
| 10 | pyridinyl |

TABLE 2-continued

Example 1: One pot Borylation/Suzuki Coupling Process

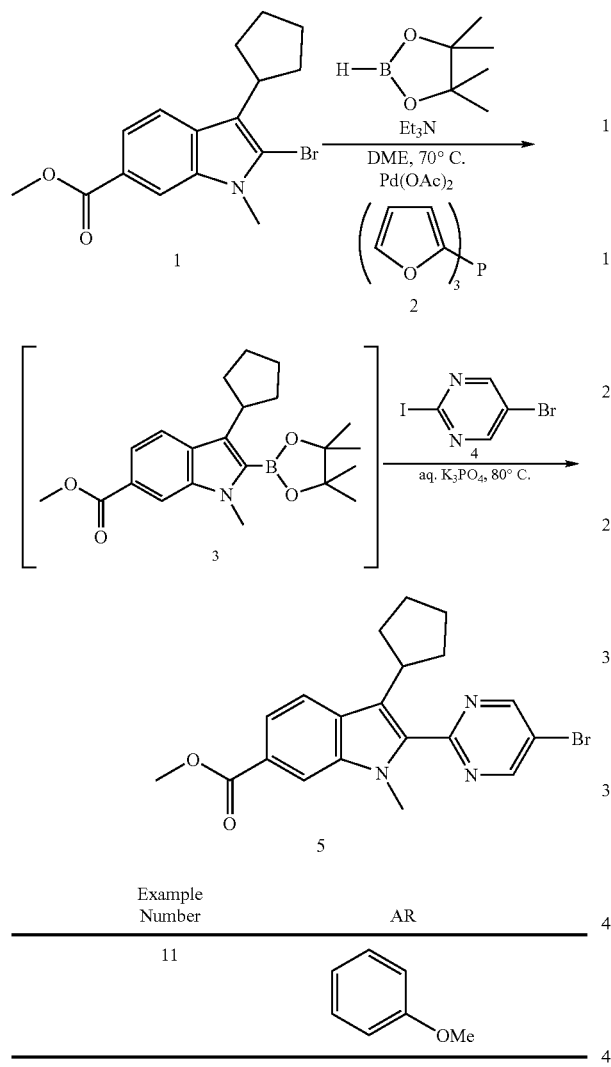

| Example Number | AR |
|---|---|
| 11 | ![phenyl-OMe] |

To a solution of the 2-bromoindole (1) (13.45 g, 40.0 mmol) in dry DME (100 mL) was added Et₃N (13.4 mL, 96.0 mmol), Tri-(2-furyl)phosphine (2) (1.11 g, 4.8 mmol, 0.12 eq) and Pd(OAc)₂ (269.4 mg, 1.2 mmol, 0.03 eq). The mixture was degasssed with N₂ and pinacolborane (14.12 mL, 94.40 mmol, 2.36 eq) was added dropwise to the mixture at r.t. The resulting mixture was heated to 70° C. and stirred at the same temperature for 16 hrs upon when the reaction was completed. The reaction mixture so obtained was directly used for the next coupling reaction.

To the reaction mixture of the pinacolate boronate (3) (20.0 mmol in 71.4 mL of DME), obtained from the borylation as described above, was charged sequentially with H₂O (11 mL, 15% of DME volume), K₃PO₄·H₂O (25.0 g, 108.56 mmol, 5.4 eq.) and 4 (6.5 g, 22.82 mmol, 1.1 eq.). The reaction mixture was warmed to 80° C. and stirred at the same temperature for about 7 hrs upon when the reaction was completed as monitored by HPLC. The reaction mixture was cooled to r.t. and quenched with 100 mL of 10% NaCl aq. solution. The mixture was then extracted with EtOAc (2×120 mL), and the combined organic layers were dried over Na₂SO₄ and rotovapored. The crude solid was slurred in 20 mL of cold acetone and then filtered off. The solid was washed further with 2 portions of cold acetone (2×10 ml) to afford 6.23 g of the product 5 as yellowish solid (75% yield, 97.9 A % purity).

$^1$H NMR (300 HMz, CDCl₃) δ 8.94 (2H, s), 8.15 (1H, s), 7.81-7.75 (2H, m), 3.96 (3H, s), 3.90 (3H, s), 3.73 (1H, m), 2.20-1.95 (6H, m), 1.74-1.71 (2H, m); $^{13}$C NMR (100 HMz, CDCl₃) δ 168.1, 158.8, 157.7, 138.2, 135.6, 129.2, 124.6, 123.4, 121.0, 119.8, 118.2, 112.6, 52.0, 36.8, 33.3, 31.9, 26.7.

Example 2

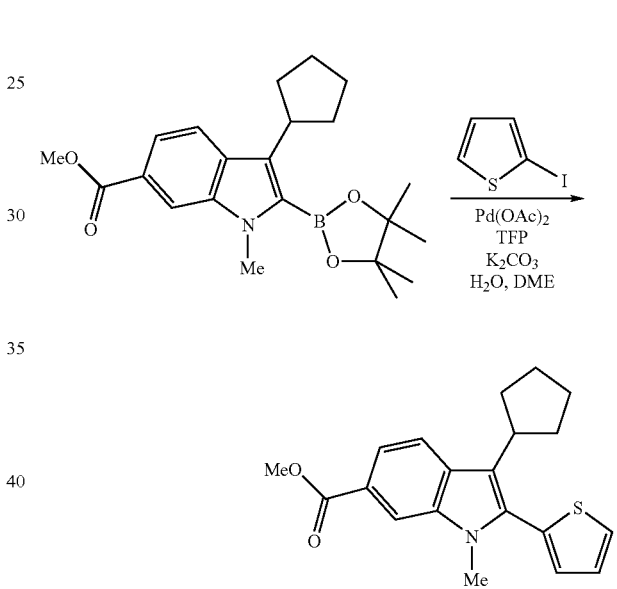

A flask was charged with pinacol borobate (383.0 mg, 1.0 mmol), 2-iodothiophene (231.0 mg, 1.1 mmol), Pd(OAc)₂ (11.2 mg, 0.05 mmol), TFP (46.4 mg, 0.2 mmol), K₂CO₃ (690.0 mg, 5 mmol), water (3 mL) and DME (2 mL). After 3 vacuum/argon cycles, the resulting mixture was heated to 80° C. 30 min later, HPLC revealed that all boronate disappeared. The area ratio of C—H, coupling product and dimer was about 3.2:92.7:4.1 on HPLC. After the reaction mixture was cooled down to room temperature, EtOAc (5 mL) was added. The aqueous layer was separated and extracted with EtOAc (2×10 mL). The combined organic extracts were washed with brine (10 mL), dried over Na₂SO₄, and concentrated in vacuo. The crude product was purified via silica gel chromatography to afford the indole (0.31 g, 91%).

$^1$H NMR (300 HMz, CDCl₃) δ 8.10 (1H, s), 7.78 (1H, d, J=6.3 Hz), 7.71 (1H, d, J=6.3 Hz), 7.49 (1H, d, J=3.9 Hz), 7.18-7.10 (1H, m), 7.09 (1H, d, J=0.9 Hz), 3.94 (3H, s), 3.64 (3H, s), 3.21 (1H, m), 2.01-1.88 (6H, m), 1.68-1.65 (2H, m);

$^{13}$C NMR (100 HMz, CDCl$_3$) δ 168.2, 137.2, 133.1, 132.0, 129.8, 129.2, 127.9, 127.3, 123.4, 120.0, 119.9, 119.8, 112.1, 52.0, 37.5, 33.5, 30.8, 26.5.

Example 3

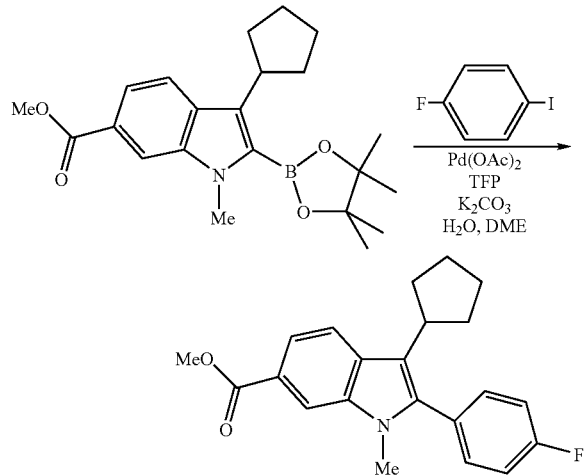

A flask was charged with pinacol borobate (383.0 mg, 1.0 mmol), 1-fluoro-4-iodobenzene (244.2 mg, 1.1 mmol), Pd(OAc)$_2$ (11.2 mg, 0.05 mmol), TFP (46.4 mg, 0.2 mmol), K$_2$CO$_3$ (690.0 mg, 5 mmol), water (3 mL) and DME (2 mL). After 3 vacuum/argon cycles, the resulting mixture was heated to 80° C. 90 min later, HPLC revealed that all boronate disappeared. The area ratio of C—H, coupling product and dimer was about 10.7:87.3:2.0 on HPLC. After the reaction mixture was cooled down to room temperature, EtOAc (5 mL) was added. The aqueous layer was separated and extracted with EtOAc (2×10 mL). The combined organic extracts were washed with brine (10 mL), dried over Na$_2$SO$_4$, and concentrated in vacuo. The crude product was purified via silica gel chromatography to afford the indole (0.28 g, 80%).

$^1$H NMR (300 HMz, CDCl$_3$) δ 8.11 (1H, s), 7.80 (1H, d, J=6.3 Hz), 7.70 (1H, d, J=6.3 Hz) 7.34-7.31 (2H, m), 7.20-7.14 (2H, m), 3.98 (3H, s), 3.55 (3H, s), 3.02 (1H, m), is 2.02-1.89 (6H, m), 1.26 (2H, bs); $^{13}$C NMR (100 HMz, CDCl$_3$) δ 168.3, 139.9, 137.0, 132.5, 132.5, 129.6, 123.0, 112.0, 119.7, 117.4, 115.7, 115.5, 112.0, 51.9, 37.4, 33.5, 30.8, 26.4.

Example 4

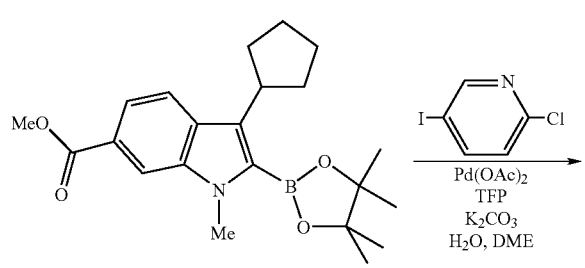

A flask was charged with pinacol borobate (383.0 mg, 1.0 mmol), 2-chloro-5-iodopyridine (263.4 mg, 1.1 mmol), Pd(OAc)$_2$ (11.2 mg, 0.05 mmol), TFP (46.4 mg, 0.2 mmol), K$_2$CO$_3$ (690.0 mg, 5 mmol), water (3 mL) and DME (2 mL). After 3 vacuum/argon cycles, the resulting mixture was heated to 80° C. 30 min later, HPLC revealed that all boronate disappeared. The area ratio of C—H, coupling product and dimer was about 8.0:90.2:1.8 on HPLC. After the reaction mixture was cooled down to room temperature, EtOAc (5 mL) was added. The aqueous layer was separated and extracted with EtOAc (2×10 mL). The combined organic extracts were washed with brine (10 mL), dried over Na$_2$SO$_4$, and concentrated in vacuo. The crude product was purified via silica gel chromatography to afford the indole (0.32 g, 86%).

$^1$H NMR (300 HMz, CDCl$_3$) δ 8.45 (1H, d, J=1.8 Hz), 8.12 (1H, s), 7.80 (1H, d, J=6.3 Hz), 7.74-7.68 (2H, m), 7.50 (1H, d, J=6.3 Hz), 3.96 (3H, s), 3.62 (3H, s), 2.98 (1H, m), 2.05-1.89 (6H, m), 1.69-1.66 (2H, m); $^{13}$C NMR (100 HMz, CDCl$_3$) δ 168.1, 151.6, 151.0, 140.5, 137.5, 135.5, 129.2, 126.8, 124.2, 123.7, 120.2, 120.0, 119.1, 112.1, 52.0, 37.3, 33.5, 31.0, 26.4.

Example 5

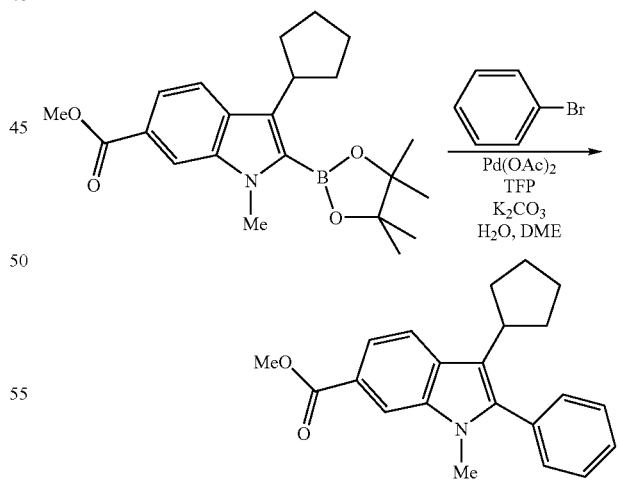

A flask was charged with pinacol borobate (383.0 mg, 1.0 mmol), bromobenzene (172.7 mg, 116 µL, 1.1 mmol), Pd(OAc)$_2$ (11.2 mg, 0.05 mmol), TFP (46.4 mg, 0.2 mmol), K$_2$CO$_3$ (690.0 mg, 5 mmol), water (3 mL) and DME (2 mL). After 3 vacuum/argon cycles, the resulting mixture was heated to 80° C. 120 min later, HPLC revealed that all boronate disappeared. The area ratio of C—H, coupling product and dimer was about 13.2:80.0:6.8 on HPLC. After the reaction mixture was cooled down to room temperature, EtOAc (5 mL) was added. The aqueous layer was separated and extracted with EtOAc (2×10 mL). The combined organic extracts were washed with brine (10 mL), dried over Na₂SO₄, and concentrated in vacuo. The crude product was purified via silica gel chromatography to afford the indole (0.25 g, 76%).

¹H NMR (300 HMz, CDCl₃) δ 8.11 (1H, s), 7.79 (1H, d, J=6.3 Hz), 7.72 (1H, d, J=6.3 Hz), 7.52-7.37 (5H, m), 3.95 (3H, s), 3.60 (3H, s), 3.07 (1H, m), 2.04-1.88 (6H, m), 1.66-1.63 (2H, m); ¹³C NMR (100 HMz, CDCl₃) δ 168.3, 141.1, 137.0, 131.9, 130.7, 129.6, 128.4, 122.8. 119.8, 119.6, 117.2, 112.0, 51.9, 37.3, 33.4, 30.9, 26.4.

Example 6

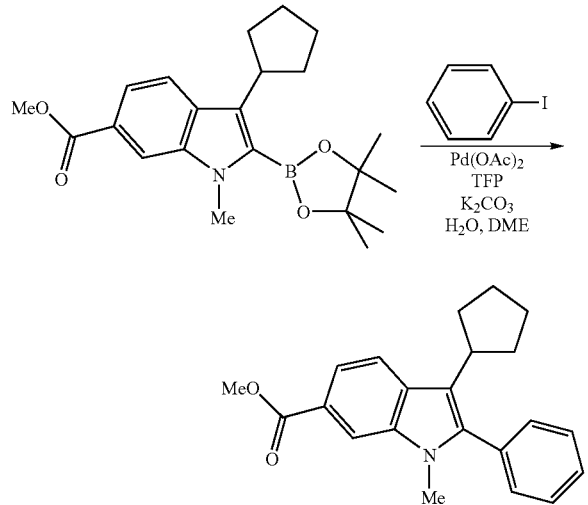

A flask was charged with pinacol borobate (383.0 mg, 1.0 mmol), iodobenzene (204.0 mg, 1.1 mmol), Pd(OAc)₂ (11.2 mg, 0.05 mmol), TFP (46.4 mg, 0.2 mmol), K₂CO₃ (690.0 mg, 5 mmol), water (3 mL) and DME (2 mL). After 3 vacuum/argon cycles, the resulting mixture was heated to 80° C. 60 min later, HPLC revealed that all boronate disappeared. The area ratio of C—H, coupling product and dimer was about 3.6:95.5:0.9 on HPLC. After the reaction mixture was cooled down to room temperature, EtOAc (5 mL) was added. The aqueous layer was separated and extracted with EtOAc (2×10 mL). The combined organic extracts were washed with brine (10 mL), dried over Na₂SO₄, and concentrated in vacuo. The crude product was purified via silica gel chromatography to afford the indole (0.30 g, 91%).

¹H NMR (300 HMz, CDCl₃) δ 8.11 (1H, s), 7.79 (1H, d, J=6.3 Hz), 7.72 (1H, d, J=6.3 Hz), 7.52-7.37 (5H, m), 3.95 (3H, s), 3.60 (3H, s), 3.07 (1H, m), 2.04-1.88 (6H, m), 1.66-1.63 (2H, m); ¹³C NMR (100 HMz, CDCl₃) δ 168.3, 141.1, 137.0, 131.9, 130.7, 129.6, 128.4, 122.8. 119.8, 119.6, 117.2, 112.0, 51.9, 37.3, 33.4, 30.9, 26.4.

Example 7

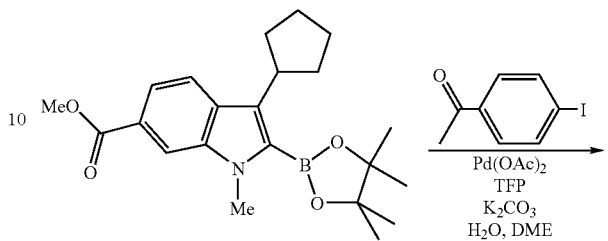

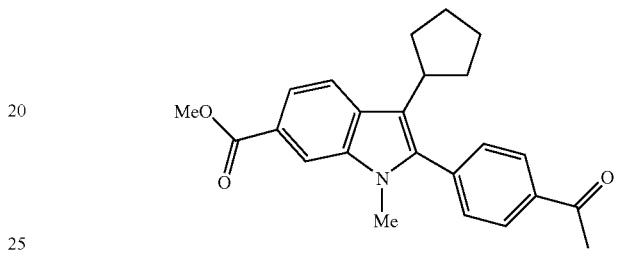

A flask was charged with pinacol borobate (383.0 mg, 1.0 mmol), 4-iodoacetophenone (270.7 mg, 1.1 mmol), Pd(OAc)₂ (11.2 mg, 0.05 mmol), TFP (46.4 mg, 0.2 mmol), K₂CO₃ (690.0 mg, 5 mmol), water (3 mL) and DME (2 mL). After 3 vacuum/argon cycles, the resulting mixture was heated to 80° C. 30 min later, HPLC revealed that all boronate disappeared. The area ratio of C—H, coupling product and dimer was about 9.1:90.3:1.6 on HPLC. After the reaction mixture was cooled down to room temperature, EtOAc (5 mL) was added. The aqueous layer was separated and extracted with EtOAc (2×10 mL). The combined organic extracts were washed with brine (10 mL), dried over Na₂SO₄, and concentrated in vacuo. The crude product was purified via silica gel chromatography to afford the indole (0.31 g, 83%).

¹H NMR (300 HMz, CDCl₃) δ 8.12-8.05 (3H, m), 7.80 (1H, d, J=6.6 Hz), 7.72 (1H, d, J=6.3 Hz), 7.50 (2H, d, J=6.0 Hz), 3.96 (3H, s), 3.62 (3H, s), 3.05 (1H, m), 2.68 (3H, s), 2.04-1.90 (6H, m), 1.67-1.64 (2H, m); ¹³C NMR (100 HMz, CDCl₃) δ 197.6, 168.2, 139.6, 137.4, 136.8, 136.6, 130.9, 129.5, 129.0, 128.4, 127.5, 123.3, 120.0, 119.9, 118.0, 112.1, 52.0, 37.3, 33.4, 31.1, 26.7, 26.4.

Example 8

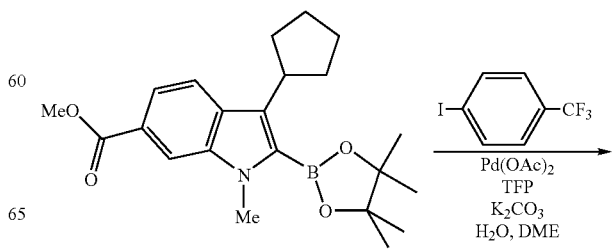

-continued

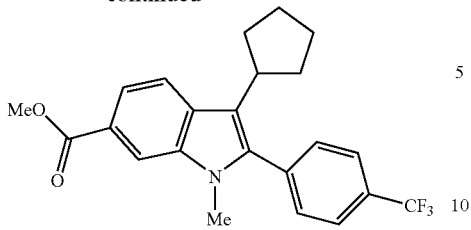

A flask was charged with pinacol borobate (383.0 mg, 1.0 mmol), 4-iodobenzotrifluoride (299.2 mg, 1.1 mmol), Pd(OAc)$_2$ (11.2 mg, 0.05 mmol), TFP (46.4 mg, 0.2 mmol), K$_2$CO$_3$ (690.0 mg, 5 mmol), water (3 mL) and DME (2 mL). After 3 vacuum/argon cycles, the resulting mixture was heated to 80° C. 30 min later, HPLC revealed that all boronate disappeared. The area ratio of C—H, coupling product and dimer was about 7.5:89.9:2.6 on HPLC. After the reaction mixture was cooled down to room temperature, EtOAc (5 mL) was added. The aqueous layer was separated and extracted with EtOAc (2×10 mL). The combined organic extracts were washed with brine (10 mL), dried over Na$_2$SO$_4$, and concentrated in vacuo. The crude product was purified via silica gel chromatography to afford the indole (0.33 g, 83%).

$^1$H NMR (300 HMz, CDCl$_3$) δ 8.13 (1H, s), 7.83-7.73 (4H, m), 7.50 (2H, J=6.0 Hz), 3.92 (3H, s), 3.59 (3H, s), 3.03 (1H, m), 2.03-1.90 (6H, m), 1.65 (2H, bs); $^{13}$C NMR (100 HMz, CDCl$_3$) δ 168.1, 139.2, 137.4, 135.6, 131.1, 129.4, 125.5, 125.4, 123.4, 120.1, 119.9, 118.1, 112.2, 51.9, 37.3, 33.5, 31.0, 26.4, 25.2.

Example 9

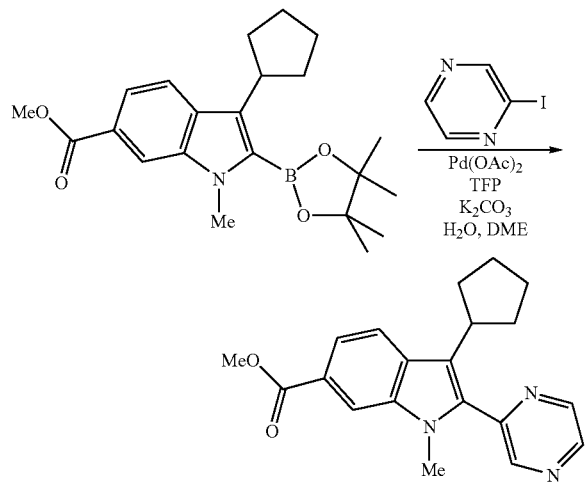

A flask was charged with pinacol borobate (383.0 mg, 1.0 mmol), iodopyrazole (226.6 mg, 1.1 mmol), Pd(OAc)$_2$ (11.2 mg, 0.05 mmol), TFP (46.4 mg, 0.2 mmol), K$_2$CO$_3$ (690.0 mg, 5 mmol), water (3 mL) and DME (2 mL). After 3 vacuum/argon cycles, the resulting mixture was heated to 80° C. 45 min later, HPLC revealed that all boronate disappeared. The area ratio of C—H, coupling product and dimer was about 3.3:85.3:11.4 on HPLC. After the reaction mixture was cooled down to room temperature, EtOAc (5 mL) was added. The aqueous layer was separated and extracted with EtOAc (2×10 mL). The combined organic extracts were washed with brine (10 mL), dried over Na$_2$SO$_4$, and concentrated in vacuo. The crude product was purified via silica gel chromatography to afford the indole (0.27 g, 81%).

$^1$H NMR (300 HMz, CDCl$_3$) δ 8.77 (2H, bs), 8.60 (1H, s), 8.16 (1H, s), 7.82-7.76 (2H, m), 3.96 (3H, s), 3.78 (3H, s), 3.20 (1H, m), 2.08-1.92 (6H, m), 1.72-1.69 (2H, m); $^{13}$C NMR (100 HMz, CDCl$_3$) δ 168.0, 147.4, 146.6, 144.4, 143.2, 138.0, 135.3, 129.0, 124.2, 120.5, 120.3, 120.0, 112.4, 52.0, 37.3, 33.6, 31.3, 26.5.

Example 10

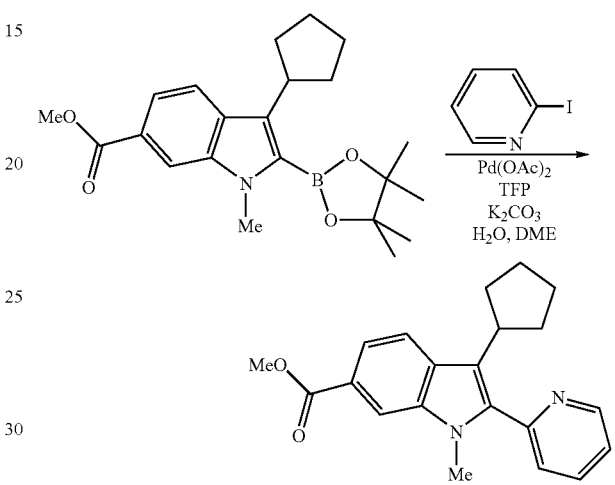

A flask was charged with pinacol borobate (383.0 mg, 1.0 mmol), 2-iodopyridine (226.6 mg, 1.1 mmol), Pd(OAc)$_2$ (11.2 mg, 0.05 mmol), TFP (46.4 mg, 0.2 mmol), K$_2$CO$_3$ (690.0 mg, 5 mmol), water (3 mL) and DME (2 mL). After 3 vacuum/argon cycles, the resulting mixture was heated to 80° C. 60 min later, HPLC revealed that all boronate disappeared. The area ratio of C—H, coupling product and dimer was about 23.5:74.2:2.3 on HPLC. After the reaction mixture was cooled down to room temperature, EtOAc (5 mL) was added. The aqueous layer was separated and extracted with EtOAc (2×10 mL). The combined organic extracts were washed with brine (10 mL), dried over Na$_2$SO$_4$, and concentrated in vacuo. The crude product was purified via silica gel chromatography to afford the indole (0.23 g, 68%).

$^1$H NMR (300 HMz, CDCl$_3$) δ 8.81 (1H, d, J=0.6 Hz), 8.14 (1H, s), 7.83-7.75 (3H, m), 7.46 (1H, d, J=5.4 Hz), 7.35 (1H, m), 3.95 (3H, s), 3.74 (3H, s), 2.04 (1H, m), 2.04-1.91 (6H, m), 1.69-1.66 (2H, m); $^{13}$C NMR (100 HMz, CDCl$_3$) δ 168.3, 151.4, 150.0, 139.1, 137.5, 136.3, 129.4, 126.2, 123.4, 122.6, 120.1, 119.7, 118.6, 112.2, 51.9, 37.3, 33.4, 31.1, 26.5.

Example 11

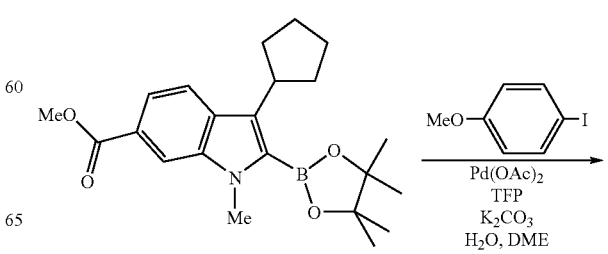

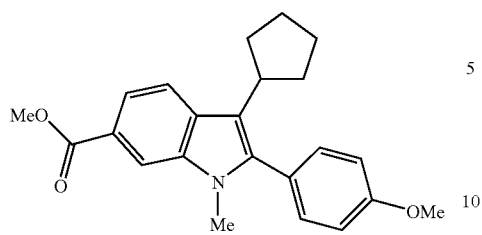

A flask was charged with pinacol borobate (766.0 mg, 2.0 mmol), 2-iodoanisole (514.9 mg, 2.2 mmol), Pd(OAc)$_2$ (22.4 mg, 0.1 mmol), TFP (92.9 mg, 0.4 mmol), K$_2$CO$_3$ (1380 mg, 10 mmol), water (6 mL) and DME (4 mL). After 3 vacuum/argon cycles, the resulting mixture was heated to 80° C. 30 min later, HPLC revealed that all boronate disappeared. The area ratio of C—H, coupling product and dimer was about 4.6:94.5:0.9 on HPLC. After the reaction mixture was cooled down to room temperature, EtOAc (5 mL) was added. The aqueous layer was separated and extracted with EtOAc (2×10 mL). The combined organic extracts were washed with brine (10 mL), dried over Na$_2$SO$_4$, and concentrated in vacuo. The crude product was purified via silica gel chromatography to afford the indole (0.64 g, 88%).

$^1$H NMR (300 HMz, CDCl$_3$) δ 8.11 (1H, s), 7.80 (1H, d, J=6.3 Hz), 7.71 (1H, d, J=6.3 Hz), 7.21 (2H, d, J=6.6 Hz), 7.00 (2H, d, J=6.3 Hz), 3.92 (3H, s), 3.83 (3H, s), 3.56 (3H, s), 3.07 (1H, m), 2.02-1.87 (6H, m), 1.65-1.62 (2H, m); $^{13}$C NMR (100 HMz, CDCl$_3$) δ 168.4, 159.8, 141.1, 136.9, 131.9, 129.7, 124.0, 122.6, 119.8, 119.5, 117.0, 114.0, 112.0, 55.3, 51.9, 37.5, 33.4, 30.8, 26.4.

Example 12

Preparation of a Bromoindole

In one embodiment, the present invention is directed to the following general multi-step synthetic method for preparing the intermediate compounds of general formula I, as set forth in Scheme I below, as well as the individual steps and intermediates set forth therein:

Condensation of the indole carboxylic acid with cyclopentanone in the presence of aqueous sodium hydroxide gave the 3-cyclopenteneyl indole carboxylic acid, which was subjected to hydrogenation in the presence of catalytic amount of palladium on carbon to afford the corresponding cyclopentyl carboxylic acid in 80% overall yield. Double methylation of the carboxylic acid and the nitrogen with methyl carbonate in NMP at 130° C. provided the N-methyl indole carboxylate methyl ester in 90% yield. Bromination of the indole carboxylate with bromine in acetonitrile furnished the 2-bromo-3-cyclopentyl indole carboxylate in 90% yield.

Example 13

Preparation of Boronate 3 Via Pd Catalyzed Borylation

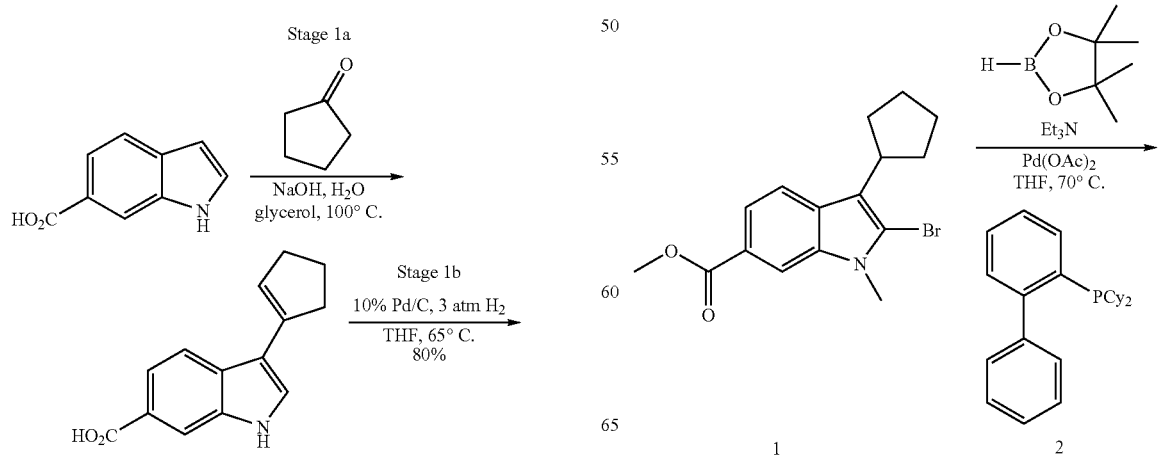

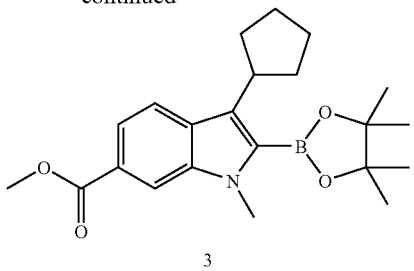

An oven dried three-neck 1 L round bottom flask fitted with condenser, temperature control, and dropping funnel was charged with bromide (50 g, 148.7 mmol), dry THF (500 ml), Et₃N (49.6 ml, 357 mmol), 2-dicyclohexylphosphinobiphenyl (2.08 g, 6 mmol) and Pd(OAc)₂ (0.33 g, 1.5 mmol). Pinacolborane (32.4 ml, 223 mmol) was added to the dropping funnel and the system was evacuated for 5-10 min and backfilled with N₂. Then pinacolborane was added dropwise to the reaction mixture and when addition was completed (ca. 30-45 min.) the mixture was heated to 60° C. until reaction was completed (HPLC monitoring).

The residue was filtered off and washed with THF (100 ml) and the filtrate was evaporated to dryness. The crude product was slurried in MeOH (200 ml) for ca 15 min and then filtered off. The cake was washed with a further portion of MeOH (100 ml) and then air dried to constant weight (53.74 g, 94%, 97 A %).

Example 14

Preparation of Boronate 3 via Br—Mg Exchange Using Magnesiate Reagents

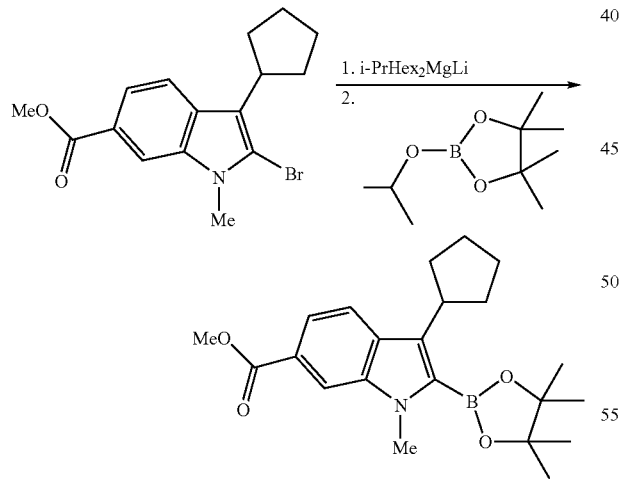

To a solution of i-PrMgCl (9.75 mL, 19.5 mmol, 2M in THF) in 22.5 mL of THF was added n-HexLi (16.96 mL, 39 mmol, 2.3M in hexane) at 0° C. The resulting mixture was stirred for 10 min. The concentration of i-Pr(n-Hex)₂MgLi solution is 0.4 M in THF.

To another flask was charged a solution of the indole bromide (33.6 g, 0.1 mol) in THF (30 mL). After the solution was cooled down to −15° C., i-Pr(n-Hex)₂MgLi was added dropwise while maintaining the internal temperature at around −15° C. The reaction completed in about 15 min after the addition.

Neat 2-isopropoxy-4,4,5,5,-tetramehthyl-1,3,2-dioxoborolane (40.8 mL, 0.2 mol) was added to the above solution at −15° C. The mixture was allowed to warm up to room temperature. After stirring 30 min at room temperature, the reaction mixture was diluted with EtOAc and aqueous NH₄Cl solution. The organic layer was separated and washed with water. Removal of the solvent gave an oily product. The oil was diluted with MeOH (about 30 mL). The solution was stirred at room temperature for a little while to form solid precipitation. The solid was collected, dried under vacuum and used for Suzuki coupling directly.

¹H NMR (300 HMz, CDCl₃) δ 8.07 (1H, s), 7.73 (1H, d, J=6.6 Hz), 7.68 (1H, d, J=6.3 Hz), 3.99 (3H, s), 3.96 (3H, s), 3.88 (1H, m), 2.02-1.94 (6H, m), 1.78-1.75 (2H, m), 1.37 (12H, s); ¹³C NMR (100 HMz, CDCl₃) δ 166.1, 137.6, 130.4, 127.2, 122.0, 118.5, 116.7, 110.2, 81.4, 49.7, 35.1, 31.8, 30.2, 24.6, 22.6.

Bromoindoles having moieties other than cyclopentyl group at the 2' position can be made using the same general procedure described above.

The invention claimed is:
1. A method comprising:
step (a) reacting a bromoindole compound of formula (vi):

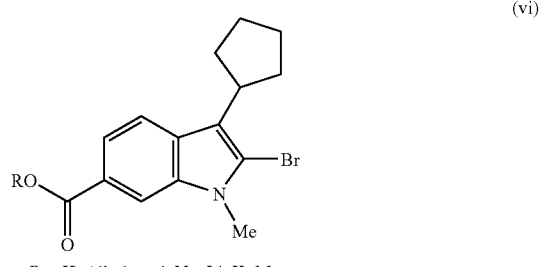

R = H, Alkyl, aryl, Na, Li, K, Mg with 4,4,5,5-tetramethyl-1,3,2-dioxaborolane, in the presence of a ligand, a palladium catalyst and a base, to provide (vii)

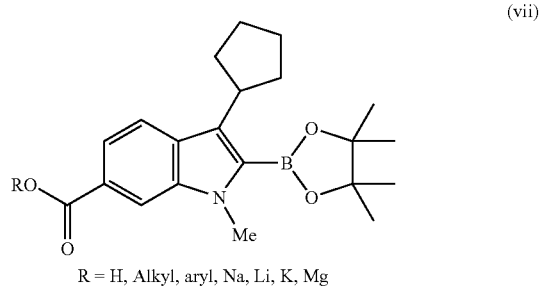

R = H, Alkyl, aryl, Na, Li, K, Mg b) reacting the product of step (a) with:

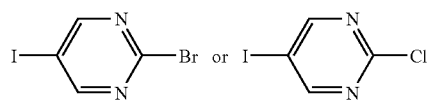

to provide (viii):

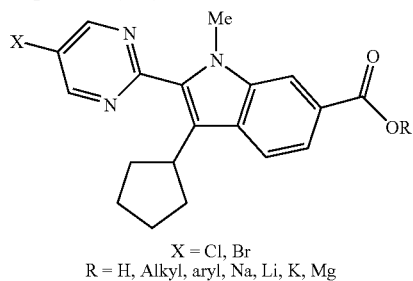

X = Cl, Br
R = H, Alkyl, aryl, Na, Li, K, Mg c) performing a hydrolysis with NaOH to provide (ix):

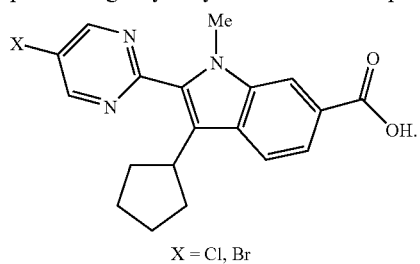

X = Cl, Br

2. The method of claim 1, wherein the ligand is chosen from tri(2-furyl)phosphine and 2-(dicyclohexylphosphino)biphenyl for the reaction of (vi) to form (vii) by the Pd-catalyzed borylation process.

3. The method of claim 1, wherein the palladium catalyst is chosen from, $Pd(OAc)_2$, $PdCl_2$, $PdBr_2$, $Pd_2(dba)_3$, $Pd_2(dba)_3 \cdot CHCl3$, $[Pd(ally)Cl]_2$, $Pd(CH_3CN)_2Cl_2$, $Pd(PhCN)_2Cl_2$, Pd/C and encapsulated Pd.

4. The method of claim 1, wherein the reaction of (vii) to form (viii) is by a Pd-catalyzed Suzuki coupling reaction in the presence of a tri(2-furyl)phosphine ligand.

5. The method of claim 1, wherein the reaction of (vi) to form (vii) is conducted in a solvent selected from DME or THF and the base is triethylamine.

6. The method of claim 1, wherein the reaction of (vii) to form (viii) is by Suzuki coupling process in the presence of a solvent which is DME, THF or 2-propanol, and in the presence of a base which is potassium phosphate or potassium carbonate.

* * * * *

UNITED STATES PATENT AND TRADEMARK OFFICE
CERTIFICATE OF CORRECTION

PATENT NO.       : 7,642,352 B2
APPLICATION NO.  : 11/351411
DATED            : January 5, 2010
INVENTOR(S)      : Ahmad Khodabocus It is certified that error appears in the above-identified patent and that said Letters Patent is hereby corrected as shown below:

In the Claims:

Column 36, line 64 claim 1 (last formula) reads:

" 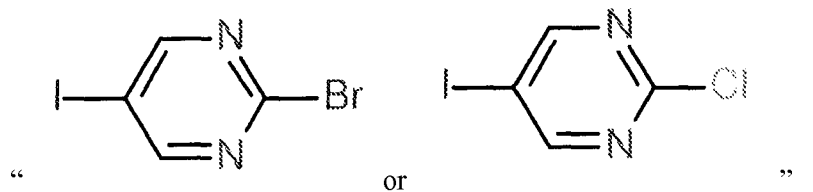 or "

Should read:

-- 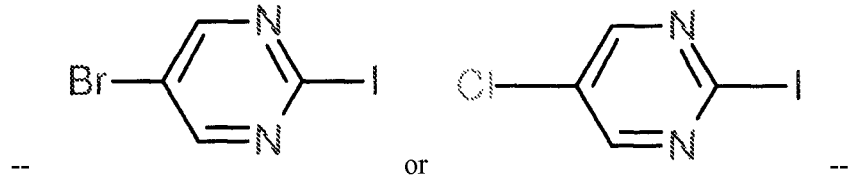 or --

Signed and Sealed this

Nineteenth Day of October, 2010

David J. Kappos
*Director of the United States Patent and Trademark Office*